(12) United States Patent
Scheiner et al.

(10) Patent No.: US 11,890,463 B2
(45) Date of Patent: Feb. 6, 2024

(54) MEDICAL LEAD FOR TREATING OBSTRUCTIVE SLEEP APNEA (OSA) WITH ELECTRICAL STIMULATION

(71) Applicant: Medtronic Xomed, Inc., Jacksonville, FL (US)

(72) Inventors: Avram Scheiner, Vadnais Heights, MN (US); Patrick W. Kinzie, Glendale, AZ (US); Randal C. Schulhauser, Phoenix, AZ (US); David C. Hacker, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 17/652,428

(22) Filed: Feb. 24, 2022

(65) Prior Publication Data

US 2022/0176106 A1    Jun. 9, 2022

Related U.S. Application Data

(62) Division of application No. 16/752,163, filed on Jan. 24, 2020, now Pat. No. 11,273,305.

(51) Int. Cl.
*A61N 1/05* (2006.01)
*A61N 1/375* (2006.01)
(Continued)

(52) U.S. Cl.
CPC ........ *A61N 1/0548* (2013.01); *A61B 17/3468* (2013.01); *A61N 1/3601* (2013.01); *A61N 1/37518* (2017.08)

(58) Field of Classification Search
CPC . A61N 1/0548; A61N 1/3601; A61N 1/37518
See application file for complete search history.

(56) References Cited

U.S. PATENT DOCUMENTS

| 5,146,918 A | 9/1992 | Kallok et al. |
| 5,540,733 A | 7/1996 | Testerman et al. |

(Continued)

FOREIGN PATENT DOCUMENTS

| EP | 3071288 B1 | 11/2018 |
| WO | 2004028618 A1 | 9/2003 |

(Continued)

OTHER PUBLICATIONS

Gharb et al., "Microsurgical Anatomy of the Terminal Hypoglossal Nerve Relevant for Neurostimulation in Obstructive Sleep Apnea," Neuromodulation: Technology at the Neural Interface, Aug. 5, 2015, 8 pp.

(Continued)

*Primary Examiner* — Eric D. Bertram
(74) *Attorney, Agent, or Firm* — Shumaker & Sieffert, P.A.

(57) ABSTRACT

A method of implanting a lead includes inserting a needle through tissue near a chin of a patient and through a tongue of the patient, inserting an introducer through an opening created by the needle, and inserting the lead through the introducer, the lead comprising an elongated member and one or more electrodes in a distal portion of the elongated member such that the one or more electrodes are implantable proximate to one or more motor points of a protrusor muscle within the tongue of the patient, wherein inserting the lead comprises inserting the lead to have a shape of one of a helix, a compound helix, a wave shape, or saw-tooth shape, or to have a loop in the lead.

15 Claims, 10 Drawing Sheets

(51) Int. Cl.
*A61B 17/34* (2006.01)
*A61N 1/36* (2006.01)

(56) References Cited

U.S. PATENT DOCUMENTS

| | | | |
|---|---|---|---|
| 5,546,952 A | 8/1996 | Erickson | |
| 5,549,655 A | 8/1996 | Erikcson | |
| 5,591,216 A | 1/1997 | Testerman et al. | |
| 6,014,589 A * | 1/2000 | Farley | A61B 18/1492 |
| | | | 606/191 |
| 6,044,297 A | 3/2000 | Sheldon et al. | |
| 6,269,269 B1 | 7/2001 | Ottenhoff et al. | |
| 6,345,202 B2 | 2/2002 | Richmond et al. | |
| 7,107,105 B2 * | 9/2006 | Bjorklund | A61N 1/056 |
| | | | 607/126 |
| 7,736,198 B2 * | 6/2010 | Bjorklund | A61N 1/056 |
| | | | 439/700 |
| 7,845,357 B2 | 12/2010 | Buscemi et al. | |
| 8,043,126 B2 * | 10/2011 | Bjorklund | A61N 1/056 |
| | | | 439/700 |
| 8,052,731 B2 * | 11/2011 | Soltis | A61N 1/057 |
| | | | 623/1.11 |
| 8,366,615 B2 | 2/2013 | Razavi | |
| 8,588,941 B2 | 11/2013 | Mashiach | |
| 8,744,589 B2 | 6/2014 | Bolea et al. | |
| 8,751,005 B2 | 6/2014 | Meadows et al. | |
| 8,813,753 B2 | 8/2014 | Bhat et al. | |
| 8,909,341 B2 | 12/2014 | Gelfand et al. | |
| 9,095,700 B2 * | 8/2015 | Kane | A61N 1/0558 |
| 9,345,416 B2 * | 5/2016 | MacAdam | A61M 25/04 |
| 9,486,628 B2 | 11/2016 | Christopherson et al. | |
| 9,643,004 B2 | 5/2017 | Gerber | |
| 9,662,045 B2 | 5/2017 | Skelton et al. | |
| 9,662,497 B2 | 5/2017 | Meadows et al. | |
| 9,757,560 B2 | 9/2017 | Papay | |
| 9,849,289 B2 | 12/2017 | Mashiach et al. | |
| 9,884,191 B2 | 2/2018 | Meadows et al. | |
| 9,888,864 B2 | 2/2018 | Rondoni et al. | |
| 9,889,299 B2 | 2/2018 | Ni et al. | |
| 9,895,541 B2 | 2/2018 | Meadows et al. | |
| 10,029,098 B2 | 7/2018 | Papay | |
| 10,065,038 B2 | 9/2018 | Papay | |
| 10,195,428 B2 | 2/2019 | Scheiner | |
| 10,363,082 B2 * | 7/2019 | Latterell | A61B 18/1492 |
| 10,744,339 B2 | 8/2020 | Makansi | |
| 10,898,709 B2 | 1/2021 | Wagner et al. | |
| 11,273,305 B2 | 3/2022 | Scheiner et al. | |
| 2002/0049479 A1 | 4/2002 | Pitts | |
| 2003/0216789 A1 | 11/2003 | Deem et al. | |
| 2004/0059404 A1 * | 3/2004 | Bjorklund | A61N 1/056 |
| | | | 607/126 |
| 2006/0292912 A1 * | 12/2006 | Bjorklund | A61N 1/056 |
| | | | 439/266 |
| 2007/0123950 A1 | 5/2007 | Ludlow et al. | |
| 2007/0173893 A1 | 7/2007 | Pitts | |
| 2008/0033421 A1 * | 2/2008 | Davis | A61B 17/0057 |
| | | | 606/41 |
| 2008/0103407 A1 | 5/2008 | Bolea et al. | |
| 2008/0161874 A1 | 7/2008 | Bennett et al. | |
| 2009/0270962 A1 | 10/2009 | Yang et al. | |
| 2010/0094379 A1 * | 4/2010 | Meadows | A61N 1/37264 |
| | | | 607/48 |
| 2010/0256719 A1 * | 10/2010 | Bjorklund | A61N 1/056 |
| | | | 607/116 |
| 2011/0270339 A1 | 11/2011 | Murray et al. | |
| 2011/0270340 A1 | 11/2011 | Pellegrini et al. | |
| 2013/0197321 A1 | 8/2013 | Wilson | |
| 2013/0204097 A1 | 8/2013 | Rondoni et al. | |
| 2013/0253309 A1 | 9/2013 | Allan et al. | |
| 2013/0253342 A1 | 9/2013 | Griswold et al. | |
| 2013/0253343 A1 | 9/2013 | Waldhauser et al. | |
| 2013/0253344 A1 | 9/2013 | Griswold et al. | |
| 2013/0253345 A1 | 9/2013 | Griswold et al. | |
| 2013/0253346 A1 | 9/2013 | Griswold et al. | |
| 2013/0253347 A1 | 9/2013 | Griswold et al. | |
| 2014/0031891 A1 | 1/2014 | Mashiach | |
| 2014/0046413 A1 * | 2/2014 | Kane | A61N 1/0558 |
| | | | 607/116 |
| 2014/0135868 A1 | 5/2014 | Bashyam | |
| 2014/0228905 A1 * | 8/2014 | Bolea | A61F 5/566 |
| | | | 607/42 |
| 2014/0323839 A1 | 10/2014 | MCCreery | |
| 2015/0100106 A1 | 4/2015 | Shishilla et al. | |
| 2015/0142120 A1 * | 5/2015 | Papay | A61N 1/3601 |
| | | | 607/42 |
| 2017/0151432 A1 | 6/2017 | Christopherson et al. | |
| 2017/0197075 A1 * | 7/2017 | Van Bruggen | A61N 1/3611 |
| 2018/0117316 A1 | 5/2018 | Wagner et al. | |
| 2018/0318577 A1 * | 11/2018 | Ng | A61N 1/0558 |
| 2020/0269044 A1 | 8/2020 | Papay | |
| 2020/0281763 A1 | 9/2020 | Scheiner | |
| 2020/0282219 A1 * | 9/2020 | Scheiner | A61N 1/36057 |
| 2020/0338358 A1 | 10/2020 | Makansi | |
| 2020/0346017 A1 | 11/2020 | Caparso et al. | |

FOREIGN PATENT DOCUMENTS

| | | |
|---|---|---|
| WO | 2005122727 A3 | 12/2005 |
| WO | 2010117810 A1 | 10/2010 |
| WO | 2017087681 A1 | 5/2017 |
| WO | 2018208992 A1 | 11/2018 |
| WO | 2019165108 A1 | 8/2019 |

OTHER PUBLICATIONS

Heiser et al., "Surgical anatomy of the hypoglossal nerve: A new classification system for selective upper airway stimulation," Wiley Online, May 22, 2017, 10 pp.

International Search Report and Written Opinion of International Application No. PCT/US2021/013666, dated May 10, 2021, 15 pp.

Medtronic, "ATTAIN STARFIX® 4195," Technical Manual, Mar. 5, 2008, accessed from https://www.accessdata.fda.gov/cdrh_docs/pdf6/P060039c.pdf, 43 pp.

Medtronic, "Basic Evaluation Procedure Technique Without Fluoroscopy—Part 3: Needle Placement," Training Video accessed from https://www.medtronic.com/us-en/healthcare-professionals/therapies-procedures/urology/sacral-neuromodulation/education-training/videos.html, webpage last updated Feb. 2018, 8 pp.

Medtronic, "Basic Evaluation Procedure Technique Without Fluoroscopy—Part 4: Test Lead Placement," Training Video accessed from https://www.medtronic.com/us-en/healthcare-professionals/therapies-procedures/urology/sacral-neuromodulation/education-training/videos.html, webpage last updated Feb. 2018, 8 pp.

Medtronic, "Basic Evaluation Procedure Technique Without Fluoroscopy—Part 5: Securing & Connecting Test Leads," Training Video accessed from https://www.medtronic.com/us-en/healthcare-professionals/therapies- procedures/urology/sacral-neuromodulation/education-training/videos.html, webpage last updated Feb. 2018, 8 pp.

Mu et al., "Human Tongue Neuroanatomy: Nerve Supply and Motor Endplates," Oct. 2010, accessed from NIH Public Access, 27 pp.

Prosecution History from U.S. Appl. No. 16/752,163, now issued U.S. Pat. No. 11,273,305, dated May 6, 2021 through Feb. 10, 2022, 47 pp.

International Preliminary Report on Patentability from International Application No. PCT/US2021/013666 dated Aug. 4, 2022, 9 pp.

* cited by examiner

MEDICAL LEAD FOR TREATING OBSTRUCTIVE SLEEP APNEA (OSA) WITH ELECTRICAL STIMULATION

This application is a divisional of U.S. patent application Ser. No. 16/752,163, filed Jan. 24, 2020, and now issued as U.S. Pat. No. 11,273,305, the entire content of which is incorporated herein by reference.

TECHNICAL FIELD

This disclosure relates to medical device systems and, more particularly, to medical device systems for delivery of electrical stimulation therapy.

BACKGROUND

Obstructive sleep apnea (OSA), which encompasses apnea and hypopnea, is a disorder in which breathing may be irregularly and repeatedly stopped and started during sleep, resulting in disrupted sleep and reduced blood oxygen levels. Muscles in a patient's throat intermittently relax thereby allowing soft tissues of the throat to obstruct the upper airway while sleeping and cause OSA. In patients with a smaller than normal airway, airflow into the upper airway can be obstructed by the tongue or soft pallet moving to the back of the throat and covering the airway. Loss of air flow also causes unusual inter-thoracic pressure as a person tries to breathe with a blocked airway. Lack of adequate levels of oxygen during sleep can contribute to abnormal heart rhythms, heart attack, heart failure, high blood pressure, stroke, memory problems, and increased accidents during the day due to inadequate sleep. Additionally, loss of sleep occurs when a person is awakened during an apneic episode.

SUMMARY

The devices, systems, and techniques of this disclosure generally relate to an implantable medical device (IMD) system and methods for therapy for obstructive sleep apnea (OSA) but can be extended to address other patient symptoms and disorders. With OSA, a patient's tongue may relax during sleep and block the patient's airway. Some example techniques to address OSA include electrically stimulating one or both hypoglossal nerves and/or motor points in the tongue of the patient. In response to the electrical stimulation, the hypoglossal nerve(s) causes protrusor muscles (e.g., genioglossus and geniohyoid muscles) to contract and move the tongue forward, thereby opening the airway. In some examples, in response to stimulating at the motor points of the protrusor muscles (e.g., a location where an axon of the hypoglossal nerve terminates at a muscle fiber), the protrusor muscles may contract to move the tongue forward, thereby opening the airway.

To stimulate the hypoglossal nerve(s) and/or motor points, a medical device outputs electrical stimulation therapy via one or more electrodes on one or more implanted leads to cause the tongue to move forward. A medical professional can implant the one or more leads into the tongue of the patient. The one or more implanted leads each include one or more electrodes coupled to the medical device (e.g., an implantable or external medical device that delivers electrical stimulation via one or more electrodes on the lead).

With lead placement in the tongue, there may be issues related to how and where to place a lead to provide effective therapy. This disclosure describes example techniques for lead structures and/or lead placement that may overcome one or more issues. Although the example techniques are described with respect to lead placement in the tongue for treating OSA, the example techniques should not be considered to be limited to lead placement in the tongue or limited to treating OSA.

As described in more detail, this disclosure describes example techniques to ensure that the lead remains in place after implantation. For example, the leads include one or more fixation members that are deployed to affix the lead in place. In one or more examples, the fixation members, when deployed, includes a bow-like member that extends outward to define a peak.

In one example, the disclosure describes a lead for delivering electrical stimulation therapy, the lead comprising an elongated member defining a longitudinal axis and comprising a proximal end and a distal end, one or more electrodes disposed at the distal end of the elongated member, a plurality of collars located along the longitudinal axis of the elongated member, and one or more fixation members, wherein at least one of the fixation members is a bow-like member having a first connection point to a first collar of the plurality of collars and a second connection point to a second collar of the plurality of collars, wherein the distal end of the elongated member is configured for insertion in a tongue of a patient such that the one or more electrodes are implanted proximate to one or more motor points of a protrusor muscle within the tongue of the patient and the bow-like member of the one or more fixation members is implanted within tissue of the tongue, and wherein the bow-like member, when deployed, defines a peak between the first connection point and the second connection point of the bow-like member, and wherein the peak is a point of the bow-like member that is furthest from the elongated member.

In one example, the disclosure describes a system for delivering electrical stimulation therapy, the system comprising a lead for delivering electrical stimulation therapy, the lead comprising an elongated member defining a longitudinal axis and comprising a proximal end and a distal end, one or more electrodes disposed at the distal end of the elongated member, a plurality of collars located along the longitudinal axis of the elongated member, and one or more fixation members, wherein at least one of the fixation member is a bow-like member having a first connection point to a first collar of the plurality of collars and a second connection point to a second collar of the plurality of collars, wherein the distal end of the elongated member is configured for insertion in a tongue of a patient such that the one or more electrodes are implanted proximate to one or more motor points of least one of a genioglossal or geniohyoid muscle within the tongue of the patient and the bow-like member of the one or more fixation members is implanted within tissue of the tongue, and wherein the bow-like member, when deployed, defines a peak between the first connection point and the second connection point of the bow-like member, and wherein the peak is a point of the bow-like member that is furthest from the elongated member, and a medical device comprising a connector assembly configured to couple to the proximal end of the elongated member of the lead, wherein the medical device is configured to deliver electrical stimulation therapy via the one or more electrodes that cause at least one of the genioglossal or geniohyoid muscle to protrude the tongue of the patient.

In one example, the disclosure describes a lead for delivering electrical stimulation therapy, the lead comprising an elongated member defining a longitudinal axis and comprising a proximal end and a distal end, wherein the elongated member has a diameter less than 1.5 millimeter (mm), one or more electrodes disposed at the distal end of the elongated member, a plurality of collars located along the longitudinal axis of the elongated member, and one or more fixation members, wherein at least one of the fixation members is a bow-like member having a first connection point to a first collar of the plurality of collars and a second connection point to a second collar of the plurality of collars, and wherein the one or more fixation members, when deployed, comprise a triangular shape or a lobe shape, wherein the distal end of the elongated member is configured for insertion in a tongue of a patient such that the one or more electrodes are implanted proximate to one or more motor points of a protrusor muscle within the tongue of the patient and the bow-like member of the one or more fixation members is implanted within tissue of the tongue, and wherein the bow-like member, when deployed, defines a peak between the first connection point and the second connection point of the bow-like member, and wherein the peak is a point of the bow-like member that is furthest from the elongated member, wherein a distance between the lead and the peak of the bow-like member is approximately 2 millimeter, and wherein a distance between the distal end of the elongated member and the bow-like member is less than or equal to 10 mm.

In one example, the disclosure describes a method of implanting a lead, the method comprising inserting a needle through tissue near a chin of a patient and through a tongue of the patient, inserting an introducer through an opening created by the needle, and inserting a lead through the introducer, the lead comprising an elongated member and one or more electrodes at a distal end of the elongated member such that the one or more electrodes are implanted proximate to one or more motor points of a protrusor muscle within the tongue of the patient, wherein inserting the lead comprises inserting the lead to have a shape of one of a helix, a compound helix, a wave shape, or saw-tooth shape, or having a loop in the lead.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
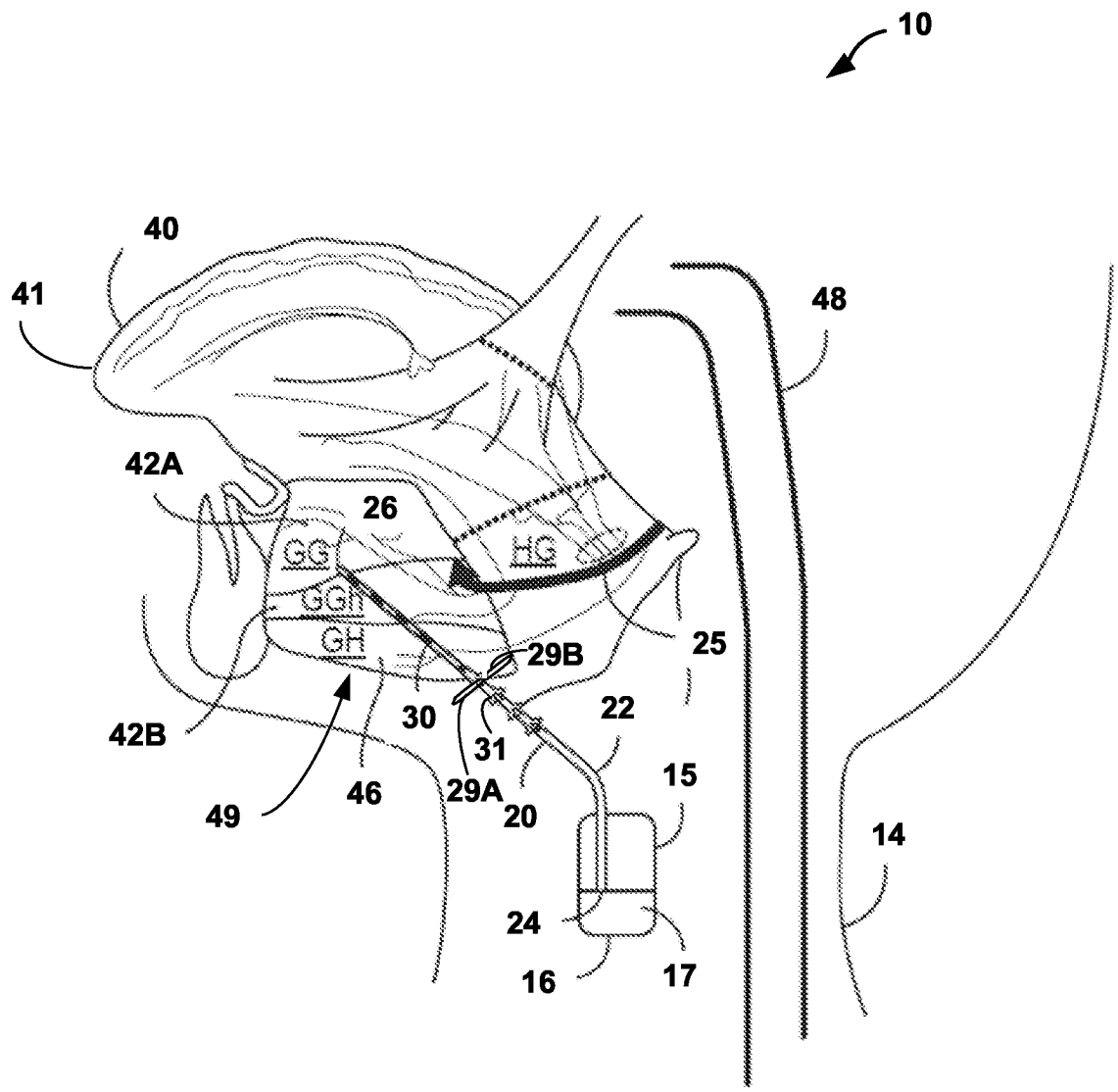
FIG. 1 is a conceptual diagram of an implantable medical device (IMD) system for delivering obstructive sleep apnea (OSA) therapy.

Medical devices, systems, and techniques for delivering electrical stimulation to the protrusor muscles of the tongue for the treatment of obstructive sleep apnea (OSA) are described in this disclosure. Electrical stimulation is delivered to cause the tongue of a patient to enter a protruded state, during sleep, to avoid or reduce upper airway obstruction. As used herein, the term, "protruded state" with regard to the tongue refers to a position that is moved forward and/or downward compared to a non-stimulated position or a relaxed position of the tongue. The protruded state is a state associated with contraction (e.g., via innervation from nerves in response to electrical stimulation) of protrusor muscles of the tongue (also sometimes referred to as "protruder" muscles of the tongue) including the genioglossus and geniohyoid muscles. A protruded state may be the opposite of a retracted and/or elevated position associated with the contraction of the retractor muscles (e.g., styloglossus and hyoglossus muscles) which retract and elevate the tongue. Electrical stimulation is delivered to cause the tongue to move (e.g., by depolarizing the nerve(s) that innervate the genioglossus and/or geniohyoid muscles) to and maintain a protruded state. As discussed above, the protruded state may prevent collapse or blockage of, open, or widen the upper airway of a patient to at least partially maintain or increase airflow (e.g., promote unrestricted airflow or at least reduced restriction of airflow during breathing).

A surgeon implants one or more leads that each include one or electrodes into the tongue such that the electrodes are proximate to a hypoglossal nerve and/or motor points (e.g., one or more locations where axons of the hypoglossal nerve terminate at respective muscle fibers of the protrusor muscles). For example, there are two hypoglossal nerves in the tongue of the patient. In one example, one lead may be used to stimulate (e.g., by delivering electrical stimulation through one or more electrodes of the lead) one of the two hypoglossal nerves, one lead may be used to stimulate both hypoglossal nerves, or two leads may be used, where each lead stimulates a respective one of the hypoglossal nerves. Stimulation of either or both hypoglossal nerves of the tongue can cause contraction of the protrusor muscles to reduce the effect of, or prevent, OSA.

There are multiple sets of motor points for each of the protrusor muscles on the left side and the right side. Each motor point may innervate one or more muscle fibers of the protrusor muscle. In one example, one lead may be used to stimulate motor points for the protrusor muscles on one side of the tongue, one lead may be used to stimulate motor points for protrusor muscles on both sides of the tongue, or two leads may be used, where each lead stimulates a respective set of motor points for the protrusor muscles on each side. Stimulation of either or both sets of motor points of the tongue can cause contraction of the protrusor muscles to reduce the effect of, or prevent, OSA.

This disclosure describes examples of techniques related to implantation of the one or more leads in the tongue for treatment of OSA. Although the example techniques are described with respect to OSA, the example techniques should not be construed as limited to OSA. Rather, the example techniques described in this disclosure may be applicable to lead implantation for treatment of various conditions including lead implantation for treatment of conditions where the lead is implanted in a location other than the tongue.

For treating OSA, once a location for implantation of a lead is selected, it may be desirable for the lead to remain implanted for many years. However, due to movement of the tongue, it may be possible for the lead to migrate forward (e.g., closer to the tip of tongue and toward the outward opening of the mouth), backward (e.g., away from the tip of tongue), or laterally (e.g., to the left or right in the tongue). This disclosure describes examples of fixation members that may be used to fix (e.g., anchor) the lead within the tongue and minimize or reduce the movement of the lead once implanted. As described in more detail, because the lead may be implanted in tissue of the tongue, such as muscle, the tongue may heal from the operation necessary for implantation. In particular, following lead implantation, the tongue may form scar tissue around the lead and the fixation member. The example fixation members described in this disclosure may leverage the natural scarring of the tissue around the fixation members to limit the movement of the lead.

In some cases, although the lead should remain implanted for many years, there may be times when it is desirable to reposition the lead or remove the lead. For example, after a trialing period is complete, due to patient discomfort, or due to other treatments for OSA, explantation of a lead may be desirable. This disclosure describes examples where the fixation members can be retracted so that it is easier to reposition the lead or remove the lead with minimal impact to the tongue. As an alternative, the fixation members may be configured to wholly or partially dissolve following implantation, likewise facilitating repositioning or removal of the lead.

Moreover, in some examples, repetitive movement of the tongue can lead to breakage of the lead. This disclosure describes examples of lead placement to allow for stress relief on the lead so that lead breakage due to tongue movement is minimized or reduced.

FIG. 1 is a conceptual diagram of a medical system for delivering OSA therapy. In system 10, implantable medical device (IMD) 16 and lead 20 are implanted in patient 14. IMD 16 includes housing 15 enclosing circuitry of IMD 16. In some examples, IMD 16 includes connector assembly 17, which is hermetically sealed to housing 15 and includes one or more connector bores for receiving a proximal end of at least one medical electrical lead 20 used for delivering OSA therapy. Although one lead 20 is illustrated in FIG. 1, there may be one or more leads 20 to which IMD 16 is coupled.

Lead 20 may include a flexible, elongate lead body 22, also called elongated member 22, that extends from lead proximal end 24 to lead distal end 26. As illustrated, lead 20 includes one or more electrodes 30 that are carried along a lead distal portion adjacent lead distal end 26 and are configured for insertion within the protrusor muscles 42A, 42B, and 46 of tongue 40. As one example, the genioglossus muscle includes oblique compartment 42A and horizontal compartment 42B. In this disclosure, the genioglossus muscle is referred to as protrusor muscle 42. Protrusor muscle 46 is an example of the geniohyoid muscle.

As illustrated, distal end 26 of lead 20 includes one or more electrodes 30. Proximal end 24 of lead 20 includes one or more electrical contacts to connect to connector assembly 17. Lead 20 also includes conductors such as coils or wires that connect respective electrodes 30 to respective electrical contacts at proximal end 24 of lead 20.

While protrusor muscles 42 and 46 are described, the example techniques described in this disclosure are not limited to stimulating protrusor muscles 42 and 46. Also, FIG. 1 illustrates one set of protrusor muscles 42 and 46 (e.g., on a first side of tongue 40). The other side of tongue 40 also includes protrusor muscles. For instance, a left side of tongue 40 includes a first set of protrusor muscles 42 and 46, and a right side of tongue 40 includes a second set of protrusor muscles.

In some examples, a surgeon may implant one or more leads 20 such that one or more electrodes 30 are implanted within soft tissue, such as musculature, proximate to medial branches of one or both hypoglossal nerves. In some examples, one or more electrodes 30 may be approximately 5 mm (e.g., 2 mm to 8 mm) from a major trunk of the hypoglossal nerve. In some examples, one or more electrodes 30 may be placed in an area of protrusor muscles 42 and 46 that include motor points, where each nerve axon terminates in the muscle (also called the neuro-muscular junction). The motor points are not at one location but spread out in the protrusor muscles. Leads 20 may be implanted such that one or more electrodes 30 may be generally in the area of the motor points (e.g., such that the motor points are within 1 to 10 mm from one or more electrodes 30). Examples of motor points for protrusor muscles 42 and 46 are illustrated in more detail with respect to FIG. 3.

Tongue 40 includes a distal end (e.g., tip of tongue 40), and electrodes 30 may be implanted proximate to root 49 of tongue 40. The surgeon may implant one or more leads 20 such that one or more electrodes are implanted proximate to root 49 of tongue 40, as illustrated in FIG. 1. For example, the location for stimulation for the genioglossus muscle 42 may be approximately 30 mm (e.g., 25 mm to 35 mm) from the Symphsis of the jaw (e.g., where the genioglossus and hypoglossal muscles insert). The location for stimulation for the geniohyoid muscle 46 may be approximately 40 mm (e.g., 35 mm to 45 mm) from the Symphsis. For both the genioglossus muscle 42 and the geniohyoid muscle 44, the location for stimulation may be approximately 11 mm (e.g., 7 mm to 15 mm) lateral to the midline on both the right and left sides of tongue 40 for stimulating respective hypoglossal nerves. In some examples, rather than stimulating hypoglossal nerves, the examples described in this disclosure may be configured for stimulating the motor points, as described in more detail with respect to FIG. 3. Stimulating the motor points may result in indirect activation of the hypoglossal nerve, but may generally be stimulating at a different location than direct stimulation to the hypoglossal nerve. As a result, in some examples, simulation of one or more motor points may result in more precise activation of muscle fibers than may be possible with stimulation of the hypoglossal nerve itself.

One or more electrodes 30 of lead 20 may be ring electrodes, segmented electrodes, partial ring electrodes or any suitable electrode configuration. Ring electrodes extend 360 degrees around the circumference of the lead body of lead 20. Segmented and partial ring electrodes each extend along an arc less than 360 degrees (e.g., 90-120 degrees) around the outer circumference of the lead body of lead 20. In this manner, multiple segmented electrodes may be disposed around the perimeter of lead 20 at the same axial position of the lead. In some examples, segmented electrodes may be useful for targeting different fibers of the same or different nerves at respective circumferential positions with respect to the lead to generate different physiological effects (e.g., therapeutic effects), permitting stimulation to be oriented directionally. In some examples, lead 20 may be, at least in part, paddle-shaped (e.g., a "paddle" lead), and may include an array of electrodes arranged as contacts or pads on a common surface, which may or may not be substantially flat and planar.

As described above, in some examples, electrodes 30 are within musculature of tongue 40. Accordingly, one or more electrodes 30 may be "intramuscular electrodes." Intramuscular electrodes may be different than other electrodes that are placed on or along a nerve trunk or branch, such as a cuff electrode, used to directly stimulate the nerve trunk or branch. The example techniques described in this disclosure are not limited to intramuscular electrodes and may be extendable to electrodes placed closer to a nerve trunk or branch of the hypoglossal nerve(s). Also, in some examples, rather than one or more electrodes 30 being "intramuscular electrodes," one or more electrodes 30 may be implanted in connective tissue or other soft tissue proximate to the hypoglossal nerve.

In some examples, lead 20 may be configured for advancement through the soft tissue, which may include the protrusor muscle tissue, to anchor electrodes 30 in proximity to the hypoglossal nerve(s) that innervate protrusor muscles 42 and/or 46 and/or motor points that connect axons of hypoglossal nerve(s) to respective muscle fibers of protrusor muscles 42 and/or 46. However, in some examples, lead 20 may be configured for advancement through vasculature of tongue 40. As one example, a surgeon may implant lead 20 in the lingual veins near the hypoglossal nerve though venous access in the subclavian vein. In such examples, one or more electrodes 30 may be "intravascular electrodes."

As described above, electrical stimulation therapy generated by IMD 16 and delivered via one or more electrodes 30 may activate protrusor muscles 42 and 46 to move tongue 40 forward, for instance, to promote a reduction in obstruction or narrowing of the upper airway 48 during sleep. As used herein, the term "activated" with regard to the electrical stimulation of protrusor muscles 42 and 46 refers to electrical stimulation that causes depolarization or an action potential of the cells of the nerve (e.g., hypoglossal nerve(s)) or stimulation at the neuro-muscular junction between the nerve and the protrusor muscles (e.g., at the motor points) innervating protrusor muscles 42 and 46 and motor points and subsequent depolarization and mechanical contraction of the protrusor muscle cells of protrusor muscles 42 and 46. In some examples, protrusor muscles 42 and 46 may be activated directly by the electrical stimulation therapy.

Protrusor muscles 42 and/or 46, on a first side of tongue 40 (e.g., the left or right side of tongue 40), may be activated by a medial branch of a first hypoglossal nerve, and the protrusor muscles, on a second side of tongue 40 (e.g., the other of the left or right side of tongue 40), may be activated by a medial branch of a second hypoglossal nerve. The medial branch of a hypoglossal nerve may also be referred to as the XIIth cranial nerve. The hyoglossus and styloglossus muscles (not shown in FIG. 1), which cause retraction and elevation of tongue 40, are activated by a lateral branch of the hypoglossal nerve.

One or more electrodes 30 may be used to deliver bilateral or unilateral stimulation to protrusor muscles 42 and 46 via the medial branch of the hypoglossal nerve or branches of the hypoglossal nerve (e.g. such as at the motor point where a terminal branch of the hypoglossal nerve interfaces with respective muscle fibers of protrusor muscles 42 and/or 46). For example, one or more electrodes 30 may be coupled to output circuitry of IMD 16 to enable delivery of electrical stimulation pulses in a manner that selectively activates the right and left protrusor muscles (e.g., in a periodic, cyclical or alternating pattern) to avoid muscle fatigue while maintaining upper airway patency. Additionally, or alternatively, IMD 16 may deliver electrical stimulation to selectively activate protrusor muscles 42 and/or 46 or portions of protrusor muscles 42 and/or 46 during unilateral stimulation of the left or right protrusor muscles.

In some examples, one lead 20 may be implanted such that one or more of electrodes 30 deliver electrical stimulation to stimulate the left hypoglossal nerve or motor points of protrusor muscles on the left side of tongue, and therefore cause the left protrusor muscles to activate. In such examples, the electrical stimulation from one or more electrodes 30 may not be of sufficient amplitude to stimulate the right hypoglossal nerve or motor points of protrusor muscles on the right side of tongue and cause the right protrusor muscles to activate. In some examples, one lead 20 may be implanted such that one or more of electrodes 30 deliver electrical stimulation to stimulate the right hypoglossal nerve or motor points of protrusor muscles on the right side of tongue, and therefore cause the right protrusor muscles to activate. In such examples, the electrical stimulation from one or more electrodes 30 may not be of sufficient amplitude to stimulate the left hypoglossal nerve or motor points of protrusor muscles on the left side of tongue and cause the left protrusor muscles to activate. Accordingly, in some examples, two leads like lead 20 may be implanted to stimulate each of the left and right hypoglossal nerves and/or motor points of respective protrusor muscles on the left and right side of tongue 40.

In some examples, one lead 20 may be implanted substantially in the middle (e.g., center) of tongue 40. In such examples, one or more electrodes 30 may deliver electrical stimulation to both hypoglossal nerves or motor points of both muscles on the both sides of tongue 40, causing both hypoglossal nerves or motor points to activate respective left and right protrusor muscles. It may be possible to utilize current steering and field shaping techniques such that one or more electrodes 30 deliver first electrical stimulation that stimulates the left hypoglossal nerve or motor points of protrusor muscles on the left side of tongue 40 with little to no stimulation of the right hypoglossal nerve or motor points of protrusor muscles on the right side of tongue 40, and then one or more electrodes 30 deliver second electrical stimulation that stimulates the right hypoglossal nerve or motor points of protrusor muscles on the right side of tongue with little to no stimulation of the left hypoglossal nerve or motor points of protrusor muscles on the left side of tongue. In examples where two leads like lead 20 are utilized, each lead may alternate delivery of stimulation to respective hypoglossal nerves or motor points. In this way, IMD 16 may stimulate one hypoglossal nerve or one set of motor points and then the other hypoglossal nerve or another set of motor points, which can reduce muscle fatigue.

For instance, continuous stimulation may cause protrusor muscles to be continuously in a protruded state. This continuous contraction may cause protrusor muscles 42 and/or 46 to fatigue. In such cases, due to fatigue, the stimulation may not cause protrusor muscles 42 and/or 46 to maintain a protruded state (or higher intensity of the electrical stimulation may be needed to cause protrusor muscles 42 and/or 46 to remain in the protruded state). By stimulating one set of protrusor muscles (e.g., left or right), a second set (e.g., other of left or right) of protrusor muscles can be at rest. Stimulation may then alternate to stimulate the protrusor muscles that were at rest and thereby maintain protrusion of tongue 40, while permitting the protrusor muscles 42 and/or 46 that were previously activated to rest. Hence, by cycling between alternate stimulation of the left and right protrusor muscles, tongue 40 can remain in the protruded state, while one of the first or second set of protrusor muscles is at rest.

In some examples, one lead 20 may be implanted laterally or diagonally across tongue 40 such that some of electrodes 30 on lead 20 can be used to stimulate the left hypoglossal nerve and/or motor points of the protrusor muscles on the left side of tongue 40 and some of electrodes 30 on the same lead 20 can be used to stimulate the right hypoglossal nerve and/or motor points of the protrusor muscles on the right side of tongue 40. In such examples, IMD 16 may selectively deliver electrical stimulation to a first hypoglossal nerve and/or first motor points of the protrusor muscles on the a first side of tongue 40 via a first set of one or more electrodes 30, and then deliver electrical stimulation to a second hypoglossal nerve and/or/or second set of motor points of the protrusor muscles on a second side of tongue 40 via a second set of one or more electrodes 30. This may be another way in which to reduce muscle fatigue.

Lead proximal end 24 includes a connector (not shown in FIG. 1) that may be coupled to connector assembly 17 of IMD 16 to provide electrical connection between circuitry enclosed by the housing 15 of IMD 16. Lead body 22 encloses electrical conductors extending from each of one or more electrodes 30 to the proximal connector at proximal end 24 to provide electrical connection between output circuitry of IMD 16 and the electrodes 30.

There may be various ways in which lead 20 is implanted in patient 14. As one example, a surgeon may insert a needle (also called introducer needle) through the lower part of the jaw and in tongue 40 starting from the back of tongue 40. The surgeon may insert the needle until a distal tip of the needle reaches a point at or adjacent to the tip of tongue 40, angling the needle to be extend proximate to the hypoglossal nerve (e.g., left or right hypoglossal nerve) and to the motor points. In some examples, the needle may include one or more electrodes (e.g., one to four electrodes) at the distal end, and the surgeon may cause the one or more electrodes of the needle to output electrical stimulation (e.g., in the form of controlled current pulses or controlled voltage pulses), which in turn causes a physiological response such as activation of protrusor muscles 42 and/or 46 and protrusion of tongue 40. The surgeon may adjust the location of the needle based on the physiological response to determine a location in tongue 40 that provides effective treatment. Using a needle with stimulating electrodes is not necessary in every example.

Once the needle is in place, the surgeon may insert a guidewire (or simply "guide") through the needle and anchor the guidewire (e.g., with tines on the guidewire) to tissue of tongue 40. Then, the surgeon may remove the needle, leaving behind the guidewire.

The surgeon may place an introducer, which may or may not include a dilator, over the guidewire through the opening created by the needle. The introducer may be referred to as an introducer, introducer sheath, or introducer/dilator. In some examples, the introducer may optionally include one or more electrodes that the surgeon can use to test stimulation of tongue 40 to ensure that lead 20 will be located in the correct location, relative to the target nerve tissue (e.g., motor points). Once the introducer is in place, the surgeon may remove the guidewire. In some examples, the introducer may be flexible or curved to ease placement of the introducer in patient 14.

The surgeon may prepare lead 20 for insertion. In some examples, there may be an additional sheath placed over lead 20 that holds fixation member(s), such as those described with respect to FIG. 2, in place. Use of such an additional sheath is not necessary in all examples. Because lead 20 may be highly flexible, in some examples, the surgeon may place a stylet through lead 20 to provide some rigidity and allow lead 20 to traverse through tongue 40 under a pushing force. Use of a stylet may not be necessary in all examples.

The surgeon may put lead 20 through the introducer such that one or more electrodes 30 are proximate to the hypoglossal nerve (e.g., such that distal end 26 is near tip of tongue as one non-limiting example). Electrodes 30 may be proximate to the hypoglossal nerve and/or motor points of the protrusor muscles due to the needle creating an opening near the hypoglossal nerve and/or motor points of the protrusor muscle. The surgeon may then tunnel proximal end 24 of lead 20 back to a connection with IMD 16.

In this manner, the surgeon may implant one lead 20. In examples where two or more leads are implanted, the surgeon may perform steps similar to those described above.

The above describes some example techniques for lead placement, and the examples described in this disclosure should not be considered limited to such examples of lead placement. Moreover, in some examples, the surgeon may use imaging techniques, such as fluoroscopy, during implantation to verify proper placement of lead 20, the needle, and/or the introducer.

FIG. 1 illustrates the location of IMD 16 as being within or proximate to the neck of patient 14. However, IMD 16 may be implanted in various other locations. As one example, the surgeon may implant IMD 16 in the left or right pectoral region. For instance, the surgeon may plan on implanting IMD 16 in the left pectoral region unless another medical device is already implanted in the left pectoral region. If another medical device is already implanted in the left pectoral region, the surgeon may then implant IMD 16 in the right pectoral region. There may other locations where the surgeon may implant IMD 16 such as the back of patient 14. The example techniques are not limited to any particular implant location of IMD 16.

In accordance with one or more examples described in this disclosure, lead 20 may be configured for implantation in tongue 40 such that post-implantation there may be little to no lead migration of lead 20. In some examples, although leaving lead 20 in place for many years after implantation may be desirable, there may be instances where adjustment or removal of lead 20 may be desired. This disclosure describes examples of lead 20 configured for adjustment and removal in a way that reduces trauma to patient 14.

Moreover, tongue 40 may move much more during the life of patient 14 as compared to other anatomy where a medical therapy lead may be implanted. Due to the relatively large number of times that tongue 40 moves, there may be a higher probability that lead 20 breaks. In some examples, lead 20 may be implanted in such a manner so as to reduce the chance of lead 20 breaking.

As described above, lead 20 is implanted to stimulate the hypoglossal nerve or motor points of the protrusor muscles. There may be certain unique challenges associated with lead 20 stimulating the hypoglossal nerve or motor points of the protrusor muscles in tongue 40 as compared to another lead being located in other portions of the body such as near the sacral nerve, spinal cord or brain or in a blood vessel. As one example, inside tongue 40, there is a chance for lead 20 to migrate proximally (e.g., towards the back of tongue 40) and distally (e.g., towards the tip of tongue 40).

To reduce the migration of lead 20, lead 20 may include one or more fixation members. The fixation members may extend outward from lead 20 and into the tissue of tongue 20. For example, FIG. 1 illustrates bow-like members 29A and 29B and one or more tines 31 located proximally on lead 20. Bow-like members 29A and 29B and one or more tines 31 are examples of the fixation members. FIG. 1 illustrates one set of bow-like members 29A and 29B configured as lobes and three tines 31. However, in some examples, there may be a plurality of bow-like members, like bow-like members 29A and 29B, and no tines. In some examples, there may be only tines 31, arranged differently than in the example of FIG. 1 to minimize lead migration.

Lead 20 may include plurality of pairs, trios, or quads of bow-like members. For instance, FIG. 1 illustrates a pair of bow-like members 29A and 29B that are axially at the same longitudinal location on lead 20. In some examples, there may be three bow-like members or four bow-like members located axially at the same longitudinal location on lead 20.

As described in more detail below, such as with respect to FIGS. 6A-6D, bow-like members 29A and 29B may each be fastened at opposite ends of respective collars located axially along elongated lead body 22. Each of the collars may be slidable along lead body 22 but one of the collars may be fixed in position. The sliding of the collars (e.g., sliding of the collars towards distal end 26) causes bow-like members 29A and 29B to extend outward to achieve an arc-like, triangle-like, or lobe-like protrusion depending on how close the collars are pushed. In some examples, the slidable collars may be limited so that bow-like members 29A and 29B, when extended, form arc-like fixation members, or so that bow-like members 29A and 29B can be extended further from forming arc-like fixation members but limited to forming triangle-like fixation members, or so that bow-like members 29A and 29B can be extended further from forming triangle-like fixation members but limited to forming lobe-like fixation members.

Once the fixation members are deployed with tissue of tongue 40, the fixation members may remain deployed due to the tissue. In some examples, the slidable collars may be locked in place so that the collars cannot slide back, unless or until the collars are intentionally slid back to retract the bow-like members flat against lead body 22.

As illustrated in FIG. 1, at least one fixation member (e.g., bow-like members 29A and 29B) are implanted within the tissue of tongue 40. Having fixation members like bow-like members 29A and 29B may be beneficial for reducing migration of lead 20. For example, after implantation and deployment of bow-like members 29A and 29B, tissue of tongue 40 may being to scar around lead 20 and/or bow-like members 29A and 29B. The scarring of the tissue of tongue 40 around bow-like members 29A and 29B may keep lead 20 in place. In other words, bow-like members 29A and 29B provide anchoring of lead 20 within tongue 40 to hold the lead in place, promote further anchoring of the lead with formation of scar tissue, and thereby reduce lead migration.

Although bow-like members 29A and 29B are illustrated as lobes, the example techniques are not so limited. Lobes may be curved bow-like members that start and return back to lead body 22, where a distance between the start and return points on lead body 22 is relatively close. However, in some examples, one or more fixation members may be triangular (e.g., not curved) or other shapes. For instance, one or more fixation members, examples of which include bow-like members 29A and 29B, extend outward to define a peak that is substantially perpendicular to the longitudinal axis of lead 20. As one example, the peak refers to an outermost location on the fixation member, relative to a longitudinal axis of lead 20, having at least two connections back to lead 20, where the tangent line at the peak is parallel to lead 20.

For example, in examples where the fixation members are bow-like members 29A and 29B, the peak may be the highest point on the curve of bow-like members 29A and 29B. In such examples, there is curve towards the peak, which forms one of the connections to lead 20, and a curve away from the peak, which forms another of the connections to lead 20. In examples where the fixation members are triangular, there may be two points on lead 20 that define a width of the triangle, and the third point connects to the two points and forms a peak.

Accordingly, lead 20 is an example of a lead for delivering electrical stimulation therapy. Lead 20 includes an elongated member (e.g., the lead body 22) defining a longitudinal axis (e.g., lengthwise axis of lead 20) that includes proximal end 24 and distal end 26. There are one or more electrodes 30 disposed at distal end 26 of the elongated member. At distal end 26 should not be interpreted to mean that there is an electrode exactly at distal end 26, although having an electrode exactly at distal end is possible. Rather, "at the distal end" means that one or more electrodes 30 are proximate to distal end 26 including possibly being exactly at distal end 26.

Lead 20, along the elongated member, also includes one or more fixation members like one or more bow-like members 29A and 29B and tines 31. However, the fixation members may only be a plurality of bow-like members, like bow-like members 29A and 29B, plurality of triangles, or some combination, and no tines 31.

In some examples, the fixation members may be held against the elongated member (e.g., in a retracted position), until the fixation members are deployed. After deployment, the fixation members extend into tissue and hold lead 20 in place (e.g., minimize lead migration). For instance, the fixation members hold lead 20 in place by bearing against tissue to provide friction or interference fit initially, and the provide an environment for scar tissue to form for long-term fixation.

For instance, distal end 26 of the elongated member is configured for insertion in tongue 40 of patient 14 such that one or more electrodes 30 are implanted proximate to one or more motor points of a protrusor muscle (e.g., protrusor muscles 42 and/or 46) within tongue 40 and at least one fixation member (e.g., one or both of bow-like members 29A and 29B) of the one or more fixation members is implanted within tissue of tongue 40. The at least one fixation member, when deployed, includes a bow-like member that defines a peak that is substantially perpendicular to the longitudinal axis of the elongated member of lead 20. "Substantially perpendicular" means that the peak is within a range of 75° to 105°, and generally at 90° relative to the longitudinal axis of the elongated member (e.g., leady body) of lead 20.

For example, the bow-like member includes a two fastening points on respective collars on lead body 22 (also called elongated member 22), as described below with respect to FIGS. 6A-6D. A line extending from a middle point that is in the middle of two fastening points on respective collars on lead body 22, that extends at substantially 90° (e.g., 75° to 105°) relative to the lead body 22, intersects the peak defined by the bow-like member.

Figure 2:
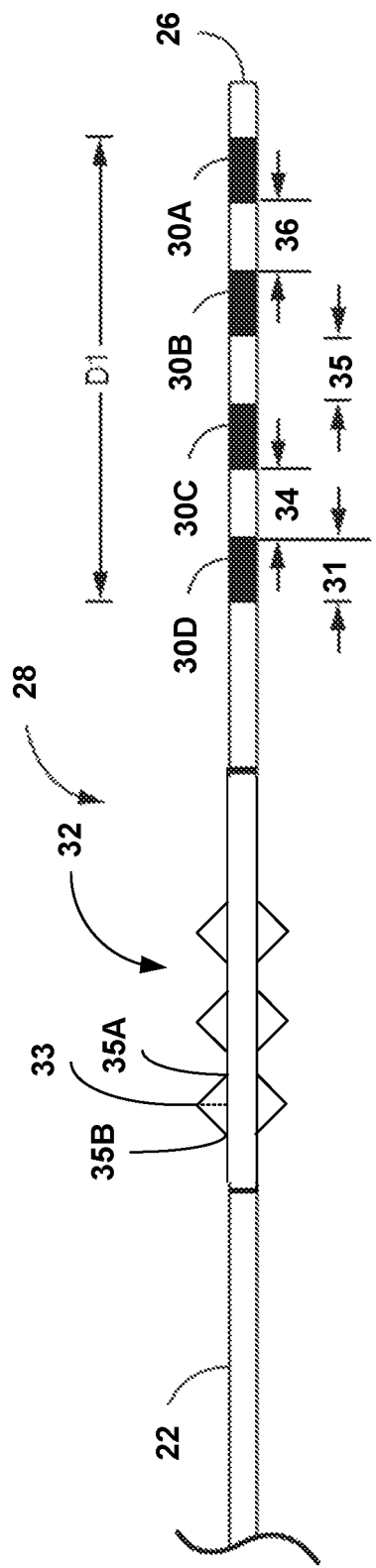
FIG. 2 is a conceptual diagram of a lead used for OSA therapy according to one or more examples of this disclosure.

FIG. 2 is a conceptual diagram of lead 20 used for OSA therapy according to one or more examples. For instance, FIG. 2 illustrates distal portion 28 of lead 20, where distal portion 28 of lead 20 may form part of lead 20 that is implanted in tongue 40, as described above. Lead 20 may include one or more electrodes 30, and FIG. 2 shows lead 20 with four electrodes 30A, 30B, 30C, and 30D (collectively referred to as "electrodes 30") spaced apart longitudinally along lead body 22. Lead body 22 is an example of the elongated member of lead 20. For instance, lead body 22 and the elongated member of lead 20 are the same.

Lead body 22 (e.g., elongated member of lead 20) may be a flexible lead body through which insulated electrical conductors extend to respective electrodes 30. The distal most electrode 30A may be adjacent or proximate to lead distal end 26. Each of electrodes 30 may be spaced proximally from the respective adjacent one of electrodes 30 by respective interelectrode distances 34, 35 and 36.

The electrical conductors that extend to respective electrodes 30 from proximal contacts at proximal end 24 may be arranged as a plurality of coils. The coils may increase the flexibility of lead 20 so that lead 20 can bend at the distal end. In some examples, the coils may be exposed along the locations of electrodes 30 such that the coils form electrodes 30. Rather than electrodes 30 being pad electrodes or ring electrodes, the coils form electrodes 30 and, in this way, electrodes 30 are bendable, providing additional flexibility. In such examples, electrodes 30 are coil electrodes.

In some examples, each one of electrodes 30 may have equivalent electrode lengths 31 (e.g., longitudinal extend of electrodes 30 along lead body 22). Lengths 31 may be approximately 3 mm, but less than 3 mm lengths are possible. However, electrodes 30 may have electrode lengths 31 that are different from each other in order (e.g., to optimize placement of the electrodes 30 or the resulting electrical field of stimulation relative to targeted stimulation sites corresponding to left and right hypoglossal nerves or branches of hypoglossal nerves and/or motor points of protrusor muscles 42 and/or 46).

Spacing 34, 35, and 36 are shown to be approximately equal in FIG. 2. However, in other examples, the interelectrode spacings 34, 35, and 36 may be different from each other (e.g., in order to optimize placement of electrodes 30 relative to the targeted stimulation sites). Spacing 34, 35, and 36 may be approximately 3 mm but less than 3 mm spacing is possible. In some examples, for a bipolar configuration, electrodes 30A and 30B form an anode and cathode pair for delivering bipolar stimulation in one portion of the protrusor muscles 42 and/or 46 (e.g., either the left or right protrusor muscles or a proximal and/or distal portion of portion of the protrusor muscles). Electrodes 30C and 30D may form a second anode and cathode pair for delivering bipolar stimulation in a different portion of protrusor muscles 42 and/or 46 (e.g., the other of the left or right portions or the other of the proximal or distal portions). Accordingly, the interelectrode spacing 35 between the two bipolar pairs 30A, 30B and 30C, 30D may be different than the interelectrode spacing 34 and 36 between the anode and cathode within each bipolar pair 30A, 30B and 30C, 30D.

In some examples, for a unipolar configuration, housing 15 of IMD 16 may include an electrode that functions as cathode, and part of the anode and cathode pair with one of electrodes 30. In some examples, housing 15 itself may function as the cathode of an anode, cathode pair, with one of electrodes 30 forming the anode. Housing 15 may be anode in some examples.

In one example, the total distance D1 encompassed by electrodes 30 along the distal portion 28 of lead body 22 may be between approximately 20 and 30 millimeters. In one example, the total distance D1 is between approximately 20 and 22 millimeters. However, as an alternative, the distances may be shorter. As one example, the distance from distal portion 28 to one or more fixation members 32 may be approximately 10 millimeters to ensure that at least one of the one or more fixation members 32 is implanted within tongue 40.

The interelectrode spacings 34 and 36 within a proximal electrode pair 30C, 30D and a distal electrode pair 30A, 30B, respectively, may be in a range of approximately 2 to 5 millimeters in some examples. The interelectrode spacing 35 separating the distal and proximal pairs 30A, 30B and 30C, 30D may be greater than the interelectrode spacings 34 and 36. For example, the interelectrode spacing 35 may be in a range of approximately 4 to 6 millimeters in some examples. In one example, each of electrodes 30 has an electrode length 31 of approximately 3 mm, and each of interelectrode spacings 34, 35 and 36 is approximately 3 mm.

In FIG. 2, each of electrodes 30 is a circumferential ring electrode which may be uniform in diameter with lead body 22. As described above, electrodes 30 may include other types of electrodes such as a tip electrode, a helical electrode, a coil electrode, as described above, segmented electrodes, a button electrode as examples. For instance, the distal most electrode 30A may be provided as a tip electrode at the lead distal end 26 with the remaining three electrodes 30B, 30C, and 30D being ring electrodes. In some examples, when electrode 30A is positioned at the distal end 26, electrode 30A may be a helical electrode configured to screw into the muscle tissue at the implant site to additionally serve as a fixation member for anchoring the distal portion 28 of lead 20 at the targeted therapy delivery site. In some examples, one or more of electrodes 30 may be a hook electrode or barbed electrode to provide active fixation of the distal portion 28 of lead 20 at the therapy delivery site.

Lead 20 may include one or more fixation members 32 for minimizing the likelihood of lead migration. In the example of FIG. 2, fixation members 32 are illustrated as triangle shaped. For example, fixation members 32, in the example of FIG. 2, may initially lay flat against lead body 22. As fixation members 32 are deployed, fixation members 32 extend outward as illustrated in FIG. 2. For instance, a first fixation member 32 may be include a first connection point 35A and a second connection point 35B to connect the first fixation member 32 to lead body 22. In some examples, first connection point 35A and second connection point 35B may be connected to respective collars, described in FIGS. 6A-6D, that are slidable along lead body 22. One collar, but not necessary the collars for first connection point 35A and second connection point 35B, may not be slidable.

As the collars are moved distally (e.g., towards electrodes 30), fixation members 32 extend outward. In some examples, such as the example illustrated in FIG. 2, fixation members 32 are bow-like members that extend outwards. For instance, in FIG. 2, fixation members 32 form triangle-like shapes when extend outwards. When the collars fully moved distally (e.g., as far as the collars are configured to move), fixation members 32 may define a peak. For example, the first fixation member 32 defines a peak 33. Peak 33 may be a point along fixation member 32 having a tangent line that is parallel with lead body 22. To form peak 33, there may be joint on fixation member 32 that is approximately in the middle of first connection point 35A and second connection point 35B. The joint moves outward in response to movement of the collars.

In some examples, a ray that extends from a point in the middle (i.e., half-way) of first connection point 35A and second connection point 35B, along lead body 22 and is substantially perpendicular to lead body 22 may intersect peak 33 (e.g., as illustrated by the dashed line). Substantially perpendicular may be in range of 75° to 105°.

Although FIG. 2 illustrates fixation members 32 as triangle-like shaped, the examples are not so limited. In some examples, fixation members 32 may be lobe-like shaped. In general, fixation members 32 may be bow-like members that extend outward in response to being deployed. Examples of the bow-like members include lobe-like members, triangle-like members, and arc-like members. In these examples, the bow-like members include a first connection point (e.g., like first connection point 35A) to a first collar and a second connection point (e.g., like second connection point 35B) to a second collar. When a pushing force, or possibly a pulling force, is applied to the bow-like members to deploy the bow-like members, the bow-like members define a peak between the first connection point and the second connection point. In some examples, the location of the peak may be at a half-way point between the first and second connection points. For instance, a ray extending from the half-way point between the first and second connection points that is substantially perpendicular to lead body 22 intersects the peak.

Fixation members 32 are shown as bow-like members (e.g., triangle-like shaped) in FIG. 2. However, there are other examples of fixation members 32. That is, at least one of fixation members 32 may be a bow-like member, and the remainder fixation members 32 may be bow-like or other shapes.

For example, fixation members 32 may include multiple sets of tines which engage the surrounding tissue when lead distal portion 28 is positioned at the target therapy delivery site. The tines of fixation member 32 may extend radially outward and proximally at an angle relative to the longitudinal axis of lead body 22 to prevent or reduce retraction of lead body 22. For instance, the tines may include springs that in an uncompressed state extend the tines outwards. Tines of fixation member 32 may be collapsible against lead body 22 when lead 20 is held within the confines of a lead delivery tool (e.g., a needle or introducer) used to deploy lead distal portion 28 at the target implant site. Upon removal of the lead delivery tool, the tines of fixation member 32 may spread to a normally extended position (e.g., due to the spring bias) to engage with surrounding tissue and resist proximal and lateral migration of lead body 22. For instance, the tines may be normally biased to the extended position but retracted against the introducer for implantation. When the introducer is removed, the tines extend outward to their uncompressed state. Examples of the tines for fixation members 32 include tines 31 of FIG. 1. In some examples, fixation member 32 may additionally or alternatively include one or more hooks, barbs, helices, or other fixation mechanisms (e.g., bow-like members) extending from one or more longitudinal locations along lead body 22 and/or lead distal end 26.

In some examples, the tines, when deployed, may be forward facing and/or backward facing. Forward facing means that the portion of the tines that are more proximate to proximal end 24 spread out when deployed. For instance, the tine has a connection point on lead body 22 and a free arm of the tine that extends away from the lead body 22, and the portion of the free arm that is more proximate to proximal end 24 extends. Backward facing means that the portion of the tines that are more proximate to distal end 26 spread out when deployed. For instance, the tine has a connection point on lead body 22 and a free arm of the tine that extends away from the lead body 22, and the portion of the free arm that is more proximate to distal end 26 extends. Having both forward and backward facing tines may reduce lateral and proximal migration.

Other examples of fixation members 32 include bow-like members 29A and 29B of FIG. 1. As described above, bow-like members 29A and 29B may be located at proximal end 24 of lead body 22 (e.g., the elongated member of lead 20) and may be implanted within tissue of tongue 40. In some examples, bow-like members 29A and 29B, when deployed, each define respective peaks between respective connection points of bow-like members 29A and 29B. The peak may be the outward most part of bow-like members 29A and 29B. For instance, a ray (e.g., hypothetical line) extending from lead body 22 and substantially perpendicular to lead body 22 intersects the peak.

In general, the one or more fixation members 32 may include at least one fixation member that is a bow-like member. The bow-like member may be implanted in tissue of tongue 40 and includes a first connection point and a second connection point to respective collars located along the longitudinal axis of lead body 22 (e.g., elongated member). As the collars move distally, the bow-like member extend outward from lead body 22 and defines a peak between the first connection point and the second connection point. For example, the peak may be halfway between the first connection point and the second connection point and extend outward from lead body 22 so that the bow-like member forms an arc, triangle, or lobe as few examples.

Fixation members 32 may partially or wholly engage one or more of protrusor muscles 42 and/or 46 and/or other muscles below tongue 40, and/or other soft tissues of the neck (e.g., fat and connective tissue), when proximal end of lead body 20 is tunneled to an implant pocket of IMD 16. In some examples, fixation member 32 may include one or more fixation mechanisms located at other locations, including at or proximate to distal end 26, between electrodes 30, or otherwise more distally or more proximally than the location shown in FIG. 2.

The implant pocket of IMD 16 may be in a pectoral region of patient 14. Lead body 22 may include proximal connectors that engage with connector assembly 17 of IMD 16. Accordingly, the length of the elongated lead body 22 from distal portion 28 to the lead proximal end 24 may be selected to extend from a target therapy delivery site in protrusor muscles 42 and/or 46 to a location in the pectoral region where IMD 16 is implanted. The length of lead body 22 (e.g., elongated member) may be up to 10 cm or up to 20 cm as examples but may generally be 25 cm or less, though longer or shorter lead body lengths may be used depending on the anatomy and size of patient 14.

Figure 3:
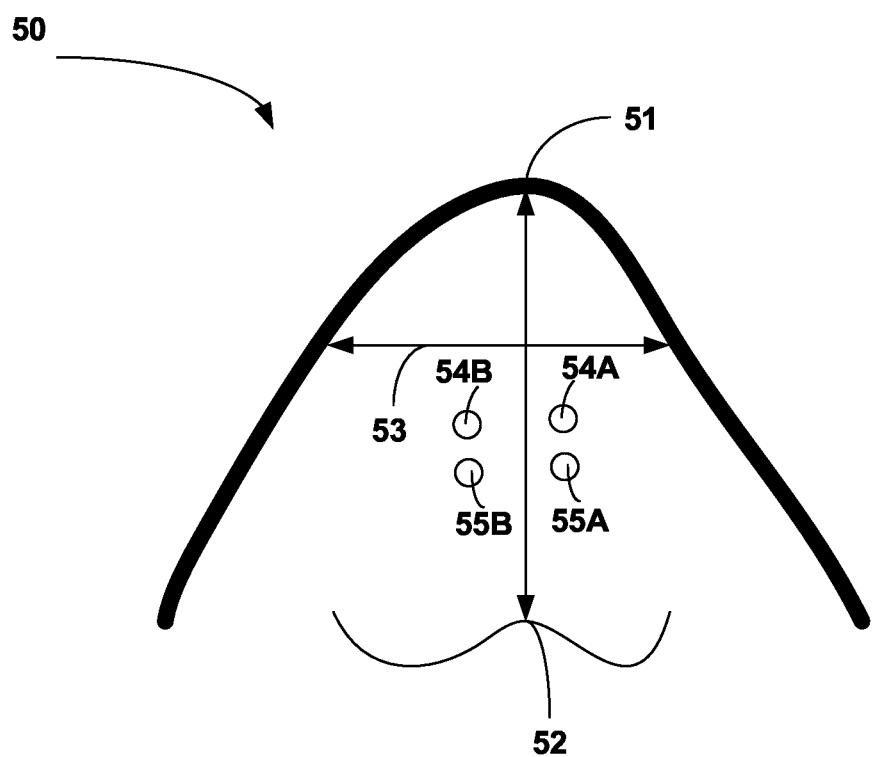
FIG. 3 is a conceptual diagram illustrating example locations of motor points where stimulation for OSA therapy may be delivered.

FIG. 3 is a conceptual diagram illustrating example locations of motor points where stimulation for OSA therapy may be delivered. FIG. 3 illustrates jaw 50 of patient 14, where patient 14 is in a supine position and jaw 50 of patient 14 is viewed from an inferior location of patient 14. For instance, FIG. 3 illustrates symphysis 51 and hyoid bone 52. In the example illustrated in FIG. 3, the line interconnecting symphysis 51 and hyoid bone 52 may be considered as a y-axis along the midline of tongue 40. FIG. 3 also illustrates intergonial distance 53 between the two gonia of patient 14, where the gonia is a point on each side of the lower jaw 50 at the mandibular angle. Intergonial distance 53 may be along the x-axis of tongue 40.

FIG. 3 illustrates motor points 54A and 54B and motor points 55A and 55B. Motor points 54A may be motor points for the right genioglossus muscle, and motor points 54B may be motor points for the left genioglossus muscle. Motor points 55A may be motor points for the right geniohyoid muscle, and motor points 55B may be motor points for the left geniohyoid muscle. Motor points 54A and 54B and motor points 55A and 55B may genericize the motor points for each muscle for purposes of illustration. There may be additional motor points and/or motor points at different locations for each muscle.

In one or more examples, lead 20 and/or one or more electrodes 30 may be implanted proximate to motor points 54A, 54B, 55A, or 55B for stimulating at motor points 54A, 54B, 55A, and/or 55B. For instance, in examples where two leads are implanted, a first lead and its electrodes may be implanted proximate to motor points 54A and/or 55A and a second lead and its electrodes may be implanted proximate to motor points 54B and/or 55B. In one or more examples, electrodes 30 may be approximately 1 mm to 10 mm from respective motor points 54A, 54B, 55A, or 55B.

A hypoglossal nerve (e.g., on the left or right side of tongue 40) initially is a trunk of nerves fibers called axons. The axons of the hypoglossal nerve branch out. For example, the trunk of hypoglossal nerve includes multiple sets of axons including a first set of axons, and the first set of axons branch out from the trunk of the hypoglossal nerve. The first set of axons include multiple groups of axons including a first group of axons, and the first group of axons branch out from the first set of axons, and so forth. The locations where the branched-out axons interface with respective muscle fibers of protrusor muscles 42 and/or 46 (e.g., genioglossus and/or geniohyoid muscle) are referred to as motor points.

For instance, a branch of the hypoglossal nerve that interfaces (e.g., connects at the neuro-muscular junction) with the muscle fiber is referred to as a terminal branch, and the end of the terminal branch is a motor point. The length of a terminal branch may be approximately 10 mm from the hypoglossal nerve to the genioglossal or geniohyoid muscles. In some examples, there may be approximately an average of 1.5 terminal branches with a standard deviation of ±0.7 for the right geniohyoid muscle, an average of 4.8 terminal branches with a standard deviation of ±1.4 for the right genioglossus muscle, an average of 2.0 terminal branches with a standard deviation of ±0.9 for the left geniohyoid muscle, and an average of 5.1 terminal branches with a standard deviation of ±1.9 for the left genioglossus muscle.

There may be possible advantages with stimulating at motor points 54A, 54B, 55A, or 55B, as compared to some other techniques. For instance, some techniques utilize cuff electrodes or stimulate at the hypoglossal nerve. Due to the different bifurcation patterns, placing a cuff electrode around the hypoglossal nerve, or generally attaching an electrode to the hypoglossal nerve can be challenging. Also, where cuff electrodes or electrodes that attach to the hypoglossal nerve are used, implanting electrodes around or at each of the hypoglossal nerves requires multiple surgical entry points to attached to both hypoglossal nerves. Moreover, utilizing cuff electrodes or electrodes that attach to the hypoglossal nerves can possibly negatively impact the nerve by tugging, stretching, or otherwise causing irritation. Accordingly, utilizing lead 20 and electrodes 30 that are implanted proximate to the motor points may be beneficial (e.g., less surgery to implant and less impact on the nerve) as compared to techniques where cuff electrodes or electrodes implanted on the hypoglossal nerve are utilized.

Furthermore, stimulating at motor points 54A, 54B, 55A, and/or 55B, such as at the bifurcation point of a motor neuron that attach to muscle fibers, may provide advantages such as for better control of muscle movement. Because motor points 54A, 54B, 55A, and 55B are spatially distributed, by stimulating motor points 54A, 54B, 55A, and/or 55B, the amount of the genioglossus and geniohyoid muscle that is being stimulated can be controlled. Also, stimulating at motor points 54A, 54B, 55A, and/or 55B may allow for more gentle muscle activation. For instance, when stimulation is provided near the trunk of the hypoglossal nerve, even stimulation signal with relatively small amplitude can cause the genioglossus and/or geniohyoid muscle to fully protrude (e.g., there is high loop gain where small stimulation amplitudes cause large muscle protrusion). Fine tuning of how much to protrude the genioglossus and/or geniohyoid muscle may not be available when stimulating at a trunk of the hypoglossal nerve. However, there may be lower loop gain stimulating at motor points 54A, 54B, 55A, and/or 55B. For instance, a stimulation signal having a lower amplitude may move cause the genioglossus and/or geniohyoid muscle to protrude a small amount, and a stimulation signal having a higher amplitude may move cause the genioglossus and/or geniohyoid muscle to protrude a higher amount when stimulating at motor points 54A, 54B, 55A and/or 55B.

The following are example locations of motor points 54A, 54B, 55A, and 55B relative to the midline (x-axis), posterior symphysis 51 (y-axis), and depth (z-axis), where the depth is from the plane formed by the inferior border of symphysis 51 and anterior border of hyoid bone 52.

Motor points 54A may be for the right genioglossus muscle and may be located at 13.48 mm±3.59 from the x-axis, 31.01 mm±6.96 from the y-axis, and 22.58 mm±3.74 from the z-axis. Motor points 55A may be for the right geniohyoid muscle and may be located at 11.74 mm±3.05 from the x-axis, 41.81 mm±6.44 from the y-axis, and 16.29 mm±3.40 from the z-axis. Motor points 54B may be for the left genioglossus muscle and may be located at 9.96 mm±2.24 from the x-axis, 29.62 mm±9.25 from the y-axis, and 21.11 mm±4.10 from the z-axis. Motor points 55B may be for the left geniohyoid muscle and may be located at 11.45 mm±1.65 from the x-axis, 39.63 mm±8.03 from the y-axis, and 15.09 mm±2.41 from the z-axis.

Figure 4:
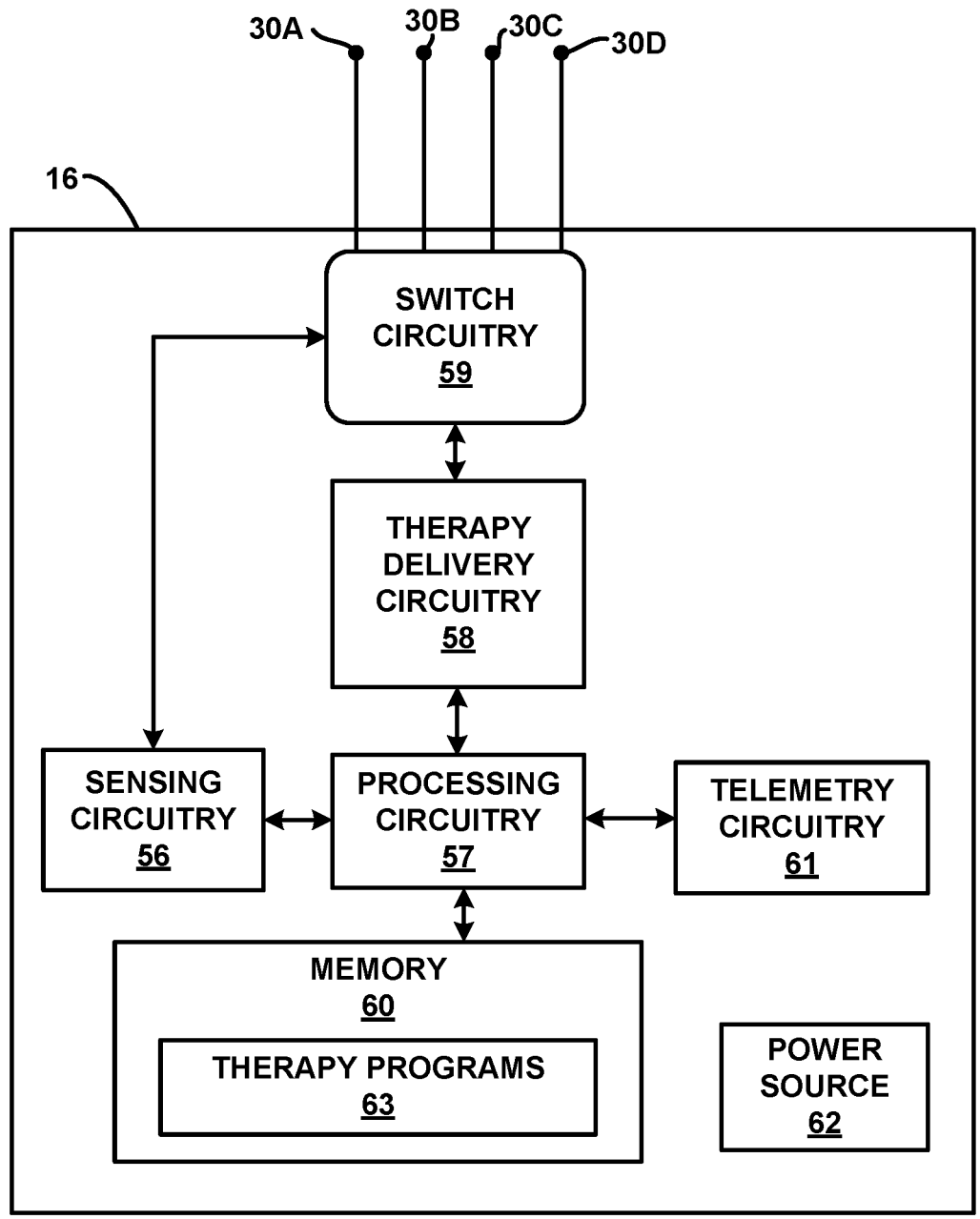
FIG. 4 is a block diagram illustrating example configurations of implantable medical devices (IMDs) which may be utilized in the system of FIG. 1.

FIG. 4 is block diagram illustrating example configurations of implantable medical devices (IMDs) which may be utilized in the system of FIG. 1. As shown in FIG. 4, IMD 16 includes sensing circuitry 56, processing circuitry 57, therapy delivery circuitry 58, switch circuitry 59, memory 60, telemetry circuitry 61, and power source 62. IMD 16 may include a greater or fewer number of components. For example, in some examples, such as examples in which IMD 16 deliver the electrical stimulation in an open-loop manner, IMD 16 may not include sensing circuitry 56.

Switch circuitry 59 may be configured to, in response to instructions from processing circuitry 57, switch the coupling of electrodes 30 between sensing circuitry 56 and therapy delivery circuitry 58. In examples where sensing circuitry 56 is not used, switch circuitry 59 may not be needed. However, even in examples where sensing circuitry 56 is not used, IMD 16 may include switch circuitry 59 such as to disconnect electrodes 30 from therapy delivery circuitry 58.

In some examples, therapy delivery circuitry 58 may include a plurality of regulated current sources or sinks, with each current source or sink coupled to one of electrodes 30. In such examples, therapy delivery circuitry 58 may control each current source or sink and switching between electrodes 30 may not be necessary for therapy delivery since each one of electrodes 30 is individually controllable.

Although not shown in FIG. 3, in some examples, IMD 16 may include one or more sensors configured to sense posture or position of patient 14. For example, IMD 16 may include accelerometer to determine if patient 14 is lying down. Another example of the one or more sensors is a motion sensor, and movement sensed by the motion sensor may indicate if patient 14 is having restless sleep, which may be indicative of the onset of OSA. Additional examples of the sensors include acoustical sensors or a microphone for detecting vibrations in upper airway 48. Vibrations in upper airway 48 may be indicative of the onset of OSA. In some examples, processing circuity 57 may control delivery of therapy based on information received from the one or more sensors, such as delivery of therapy after sensing an onset of OSA.

In some examples, electrodes 30 may be configured to sense electromyogram (EMG) signals. Sensing circuitry 56 may be switchably coupled to electrodes 30 via switch circuitry 59 to be used as EMG sensing electrodes with electrodes 30 are not being used for stimulation. EMG signals may be used by processing circuitry 57 to detect sleep state and/or low tonal state of protrusor muscles 42 and/or 46 for use in delivering electrical stimulation. In some examples, rather than using electrodes 30 or in addition to using electrodes 30, there may be other electrodes or sensors used to sense EMG signals.

In general, IMD 16 may comprise any suitable arrangement of hardware, alone or in combination with software and/or firmware, to perform the techniques attributed to IMD 16 and processing circuitry 57, therapy delivery circuitry 58, and telemetry circuitry 61 of IMD 16. In various examples, IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components.

The various units of IMD 16 may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, one or more of the units may be distinct circuit blocks (fixed-function or programmable), and in some examples, one or more of the units may be integrated circuits.

IMD 16 may include arithmetic logic units (ALUs), elementary function units (EFUs), digital circuits, analog circuits, and/or programmable cores, formed from programmable circuits. In examples where the operations of IMD 16 are performed using software executed by the programmable circuits, memory 60 may store the instructions (e.g., object code) of the software that processing circuitry 57 receives and executes, or another memory within IMD 16 (not shown) may store such instructions.

IMD 16 also, in various examples, may include a memory 60, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although sensing circuitry 56, processing circuitry 57, therapy delivery circuitry 58, switch circuitry 59, and telemetry circuitry 61 are described as separate circuitry, in some examples, sensing circuitry 56, processing circuitry 57, therapy delivery circuitry 58, switch circuitry 59, and telemetry circuitry 61 are functionally integrated. In some examples, sensing circuitry 56, processing circuitry 57, therapy delivery circuitry 58, switch circuitry 59, and telemetry circuitry 61 correspond to individual hardware units, such as ASICs, DSPs, FPGAs, or other hardware units.

Memory 60 stores therapy programs 63 (also called stimulation programs 63) that specify stimulation parameter values for the electrical stimulation provided by IMD 16. Memory 60 may also store instructions for execution by processing circuitry 57, in addition to stimulation programs 63. Information related to sensed parameters of patient 14 (e.g., from sensing circuitry 56 or the one or more sensors of IMD 16) may be recorded for long-term storage and retrieval by a user, and/or used by processing circuitry 57 for adjustment of stimulation parameters (e.g., amplitude, pulse width, and pulse rate). In some examples, memory 60 includes separate memories for storing instructions, electrical signal information, and stimulation programs 63. In some examples, processing circuitry 57 may select new stimulation parameters for a stimulation program 63 or new stimulation program from stimulation programs 63 to use in the delivery of the electrical stimulation based on patient input and/or monitored physiological states after termination of the electrical stimulation.

Generally, therapy delivery circuitry 58 generates and delivers electrical stimulation under the control of processing circuitry 57. In some examples, processing circuitry 57 controls therapy delivery circuitry 58 by accessing memory 60 to selectively access and load at least one of therapy programs 63 to therapy delivery circuitry 58. For example, in operation, processing circuitry 57 may access memory 60 to load one of stimulation programs 63 to therapy delivery circuitry 58.

By way of example, processing circuitry 57 may access memory 60 to load one of stimulation programs 63 to control therapy delivery circuitry 58 for delivering the electrical stimulation to patient 14. A clinician or patient 14 may select a particular one of stimulation programs 63 from a list using a programming device, such as a patient programmer or a clinician programmer. Processing circuitry 57 may receive the selection via telemetry circuitry 61. Therapy delivery circuitry 58 delivers the electrical stimulation to patient 14 according to the selected program for an extended period of time, such as minutes or hours while patient 14 is asleep (e.g., as determined from the one or more sensors and/or sensing circuitry 56). For example, processing circuitry 57 may control switch circuitry 59 to couple electrodes 30 to therapy delivery circuitry 58.

Therapy delivery circuitry 58 delivers electrical stimulation according to stimulation parameters. In some examples, therapy delivery circuitry 58 delivers electrical stimulation in the form of electrical pulses. In such examples, relevant stimulation parameters may include a voltage or current pulse amplitude, a pulse rate, a pulse width, a duty cycle, and/or the combination of electrodes 30 that therapy delivery circuitry 58 uses to deliver the stimulation signal. In some examples, therapy delivery circuitry 58 delivers electrical stimulation in the form of continuous waveforms. In such examples, relevant stimulation parameters may include a voltage or current amplitude, a frequency, a shape of the stimulation signal, a duty cycle of the stimulation signal, or the combination of electrodes 30 therapy delivery circuitry 58 uses to deliver the stimulation signal.

In some examples, the stimulation parameters for the stimulation programs 63 may be selected to cause protrusor muscles 42 and/or 46 to a protruded state (e.g., to open-up airway 48). An example range of stimulation parameters for the electrical stimulation that are likely to be effective in treating OSA (e.g., upon application to the hypoglossal nerves to cause protrusor muscles 42, 46 to protrude or upon application to motor points such as motor points 54A, 54B, 55A, and 55B), are as follows:

a. Frequency or pulse rate: between about 30 Hz and about 50 Hz. In some examples, the minimum target frequency is used which can achieve muscle tetany (e.g., constant contraction) and provide the required force to open the airway.

b. Current Amplitude: between about 0.5 milliamps (mA) and about 10 mA, and more generally from 0.5 mA to 3 mA, and approximately 1.5 mA.

c. Pulse Width: between about 100 microseconds (μs) and about 500 μs. In some examples, a pulse width of 150 μs might be used for reduced power consumption. In some particular examples, the pulse width is approximately 210 μs. In some cases, shorter pulse widths may be used in conjunction with higher current or voltage amplitudes.

Processing circuitry 57 may select stimulation programs 63 for alternating delivery of electrical stimulation between stimulating the left protrusor muscles 42 and/or 46 and the right protrusor muscles 42 and/or 46 on a time basis, such as in examples where two leads 20 are implanted. In some examples, there may be some overlap in the delivery of electrical stimulation such that for some of amount of time both left and right protrusor muscles 42 and/or 46 are being stimulated. In some examples, there may be a pause in alternating stimulation (e.g., stimulate left protrusor muscles, a time period with no stimulation, then stimulate right protrusor muscles, and so forth). Processing circuitry 57 may also select stimulation programs 63 that select between different combinations of electrodes 30 for stimulating, such as to stimulate different locations of the hypoglossal nerve(s), which may help with fatigue as well as provide more granular control of how much to protrude tongue 40.

In the example of FIG. 4, therapy delivery circuitry 58 drives electrodes 30 of lead 20. Specifically, therapy delivery circuitry 58 delivers electrical stimulation (e.g., regulated current or voltage pulses at pulse rates and pulse widths described above) to tissue of patient 14 via selected electrodes 30A-30D carried by lead 20. A proximal end of lead 20 extends from the housing of IMD 16 and a distal end of lead 20 extends to a target therapy site, such as one or both hypoglossal nerves and/or motor points 54A, 55A, 54B, and/or 55B. Therapy delivery circuitry 54 may deliver electrical stimulation with electrodes on more than one lead and each of the leads may carry one or more electrodes, such as when patient 14 is implanted with two leads 20 in tongue 40 for stimulating both hypoglossal nerves simultaneously or bilaterally (e.g., one after the other) or both motor points 54A and 54B and/or motor points 55A and 55B. The leads may be configured as an axial lead with ring electrodes or segmented electrodes and/or paddle leads with electrode pads arranged in a two-dimensional array. The electrodes may operate in a bipolar or multi-polar configuration with other electrodes, or may operate in a unipolar configuration referenced to an electrode carried by the device housing or "can" of IMD 16.

In this way, the example of FIG. 4 may be considered as a system for delivering electrical stimulation therapy that includes lead 20 for delivering electrical stimulation therapy. Rather than lead 20 or in addition to lead 20, in some examples, lead 90, described in more detail with respect to FIGS. 6A-6D, may be utilized. Whether lead 20 or lead 90 is used, the lead includes an elongated member (e.g., lead body 22 or elongated member 93 of FIGS. 6A-6D) defining a longitudinal axis and including a proximal end and a distal end. The lead also includes one or more electrodes disposed at the distal end of the elongated member and one or more fixation members (e.g., fixation members 32 or fixation members 100A-100F described with FIGS. 6A-6D).

The distal end of the elongated member is implanted in tongue 40 of patient 14 such that the one or more electrodes are implanted proximate to one or more motor points (e.g., motor points 54A, 54B, 55A, and/or 55B) of a protrusor muscle (e.g., at least one of the genioglossus or geniohyoid muscle) of tongue 40 of patient 14 and at least one fixation member of the one or more fixation members is a bow-like member that is implanted within tissue of tongue 40. At least one fixation member, when deployed, includes a peak between connection points of the bow-like member.

A medical device (e.g., IMD 16) may include connector assembly 17 configured to couple to the proximal end of the elongated member of the lead. The medical device may be configured to deliver electrical stimulation therapy via the one or more electrodes that cause at least one of the genioglossal or geniohyoid muscle (e.g., protrusor muscles 42 and/or 46) to protrude tongue 40 of patient 14.

In the above example, the medical device is coupled to one lead (e.g., lead 20 or lead 90, described below). However, the example techniques are not so limited. In some examples, patient 14 may be implanted with two leads, where a first lead is for stimulating a first set of motor points (e.g., motor points 54A and/or 55A) of a first protrusor muscle of tongue 40 and the second lead is for stimulating a second set of motor points (e.g., motor points 54B and/or 55B) of a second protrusor muscle of tongue 40. One or both of the first and second leads may be similar to leads 20 and 90. For example, the second lead may include a second elongated member defining a second longitudinal axis including a second proximal end and a second distal end, a second set of one or more electrodes disposed at the distal end of the second elongated member, and a second set of one or more fixation members.

The second distal end of the second elongated member is implanted in tongue 40 of patient 14 such that the one or more electrodes are implanted proximate to a second set of motor points of a second protrusor muscle within tongue 40 of patient 14 and at least one fixation member of the second set of one or more fixation members is implanted within tissue of tongue 40, and at least one fixation member of the second set of one or more fixation members, when deployed, defines a peak between connection points of the connection points of the at least one fixation member (e.g., a bow-like member).

In some examples, processing circuitry 57 may control therapy delivery circuitry 58 to deliver or terminate the electrical stimulation based on patient input received via telemetry circuitry 61. Telemetry circuitry 61 includes any suitable hardware, firmware, software or any combination thereof for communicating with another device, such as an external programmer. Under the control of processing circuitry 57, telemetry circuitry 61 may receive downlink telemetry (e.g., patient input) from and send uplink telemetry (e.g., an alert) to a programmer with the aid of an antenna, which may be internal and/or external. Processing circuitry 57 may provide the data to be uplinked to the programmer and the control signals for telemetry circuitry 61 and receive data from telemetry circuitry 61.

Generally, processing circuitry 57 controls telemetry circuitry 61 to exchange information with a medical device programmer and/or another device external to IMD 16. Processing circuitry 57 may transmit operational information and receive stimulation programs or stimulation parameter adjustments via telemetry circuitry 61. Also, in some examples, IMD 16 may communicate with other implanted devices, such as stimulators, control devices, or sensors, via telemetry circuitry 61.

Power source 62 delivers operating power to the components of IMD 16. Power source 62 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever electrical stimulation is to occur.

Figure 5:
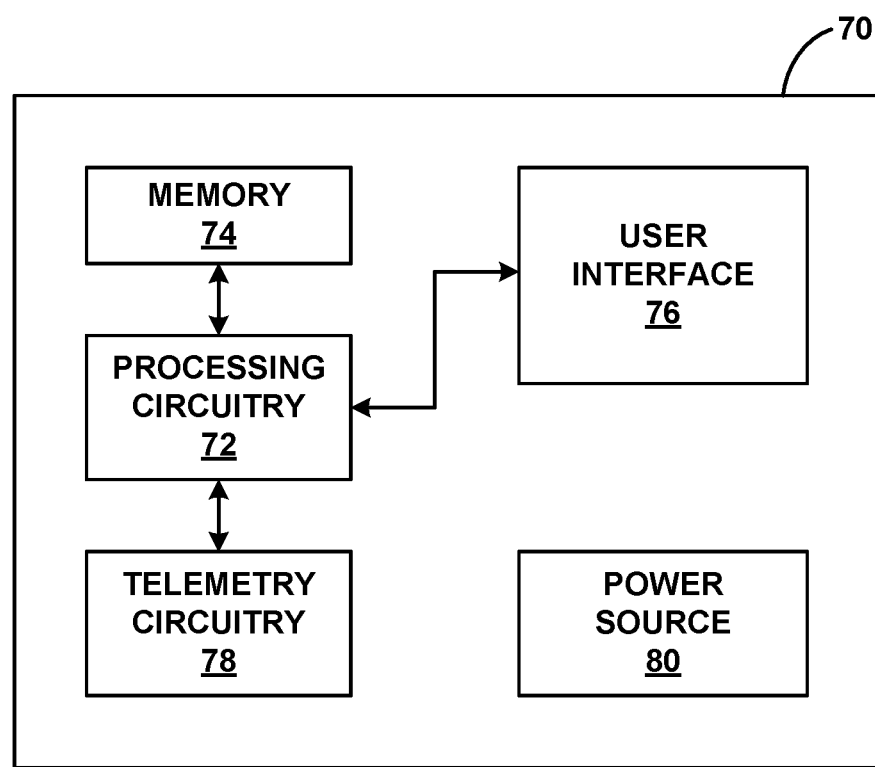
FIG. 5 is a block diagram illustrating an example configuration of an external programmer.

FIG. 5 is a block diagram illustrating an example configuration of an external programmer 70. While programmer 70 may generally be described as a hand-held computing device, the programmer may be a notebook computer, a cell phone, or a workstation, for example. As illustrated in FIG. 5, external programmer 70 may include processing circuitry 72, memory 74, user interface 76, telemetry circuitry 78, and power source 80.

In general, programmer 70 comprises any suitable arrangement of hardware, alone or in combination with software and/or firmware, to perform the techniques attributed to programmer 70, and processing circuitry 72, user interface 76, and telemetry module 78 of programmer 70. Examples of processing circuitry 72 may include one or more processors, such as one or more microprocessors, DSPs, ASICs, FPGAs, or any other equivalent integrated or discrete logic circuitry, as well as any combinations of such components. Examples of memory 74 include RAM, ROM, PROM, EPROM, EEPROM, flash memory, a hard disk, a CD-ROM, comprising executable instructions for causing the one or more processors to perform the actions attributed to them. Moreover, although processing circuitry 72 and telemetry circuitry 78 are described as separate circuitry, in some examples, processing circuitry 72 and telemetry circuitry 78 are functionally integrated. In some examples, processing circuitry 72 and telemetry circuitry 78 correspond to individual hardware units, such as ASICs, DSPs, FPGAs, or other hardware units.

In some examples, memory 74 may further include program information (e.g., stimulation programs) defining the electrical stimulation, similar to those stored in memory 60 of IMD 16. The stimulation programs stored in memory 74 may be downloaded into memory 60 of IMD 16.

User interface 76 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processing circuitry 72 may present and receive information relating to electrical stimulation and resulting therapeutic effects via user interface 76. For example, processing circuitry 72 may receive patient input via user interface 76. The input may be, for example, in the form of pressing a button on a keypad or selecting an icon from a touch screen.

Processing circuitry 72 may also present information to the patient in the form of alerts related to delivery of the electrical stimulation to patient 14 or a caregiver via user interface 76. Although not shown, programmer 70 may additionally or alternatively include a data or network interface to another computing device, to facilitate communication with the other device, and presentation of information relating to the electrical stimulation and therapeutic effects after termination of the electrical stimulation via the other device.

Telemetry circuitry 78 supports wireless communication between IMD 16 and programmer 70 under the control of processing circuitry 72. Telemetry circuitry 78 may also be configured to communicate with another computing device via wireless communication techniques, or direct communication through a wired connection. In some examples, telemetry circuitry 78 may be substantially similar to telemetry circuitry 61 of IMD 16 described above, providing wireless communication via an RF or proximal inductive medium. In some examples, telemetry circuitry 78 may include an antenna, which may take on a variety of forms, such as an internal or external antenna.

Examples of local wireless communication techniques that may be employed to facilitate communication between programmer 70 and another computing device include RF communication according to the 802.11 or Bluetooth specification sets, infrared communication (e.g., according to the IrDA standard), or other standard or proprietary telemetry protocols. In this manner, other external devices may be capable of communicating with programmer 70 without needing to establish a secure wireless connection.

Power source 80 delivers operating power to the components of programmer 70. Power source 80 may include a battery and a power generation circuit to produce the operating power. In some examples, the battery may be rechargeable to allow extended operation.

FIGS. 6A-6D are conceptual diagrams illustrating deployment of fixation members. For example, FIGS. 6A-6D illustrate an example of lead 90 that includes elongated member 93 (e.g., lead body) defining a longitudinal axis 92 and includes proximate end 96 and distal end 94. In the example of FIGS. 6A-6D, one or more electrodes 98A and 98B are disposed at distal end 94, and one or more proximal contacts 99A and 99B are disposed at proximal end 96 for connection to IMD 16. In some examples, there may be a 1 mm spacing between electrode 98A and distal end 94, and "disposed at distal end 94" includes examples where the one or more electrodes 98A and 98B are proximate to distal end 94.

Figures 6A, 6B, 6C, 6D:
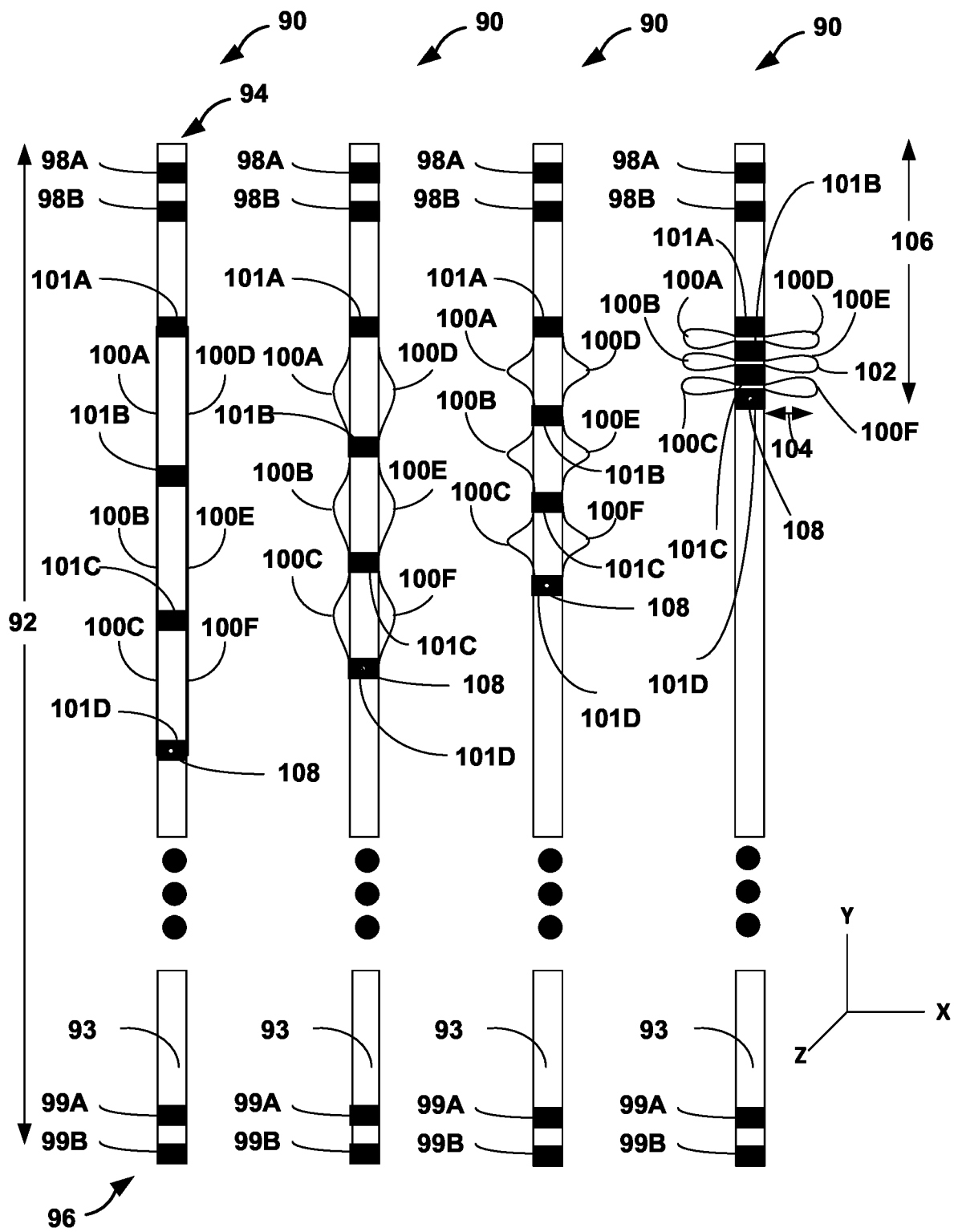
FIGS. 6A-6D are conceptual diagrams illustrating deployment of fixation members.

As illustrated in FIGS. 6A-6D, lead 90 includes one or more fixation members 100A-100F. Fixation members 100A-100F may be in an undeployed state, where fixation members 100A-100F rest generally flat in an undeployed (i.e., retracted) state along elongated member 93, as illustrated in FIG. 6A. As described in more detail below, FIG. 6B illustrates fixation members 100A-100F in a first partially deployed (i.e., partially extended) state, and FIG. 6C illustrates fixation members 100A-100F in a second partially deployed (i.e., partially extended) state. FIG. 6D illustrates fixation members 100A-100F in a fully deployed state (i.e., fully extended). As described in more detail, fixation members 100A-100F may be bow-like members that can be selectively extended from a flat configuration, to an arc-like configuration, to a triangle-like configuration, and ultimately to a lobe-like configuration, and retracted from the lobe-like configuration, to a triangle-like configuration, to the arc-like configuration, and to the flat configuration.

As illustrated in FIGS. 6A-6D, lead 90 includes one or more collars 101A-101D. Each one of collars 101A-101D forms a connection point for at least one of fixation members 100A-100F. Collars 101A-101D and fixation members 100A-100F may be formed from polyurethane, silicone, polytetrafluoroethylene (PTFE), silicone rubber, nylon, polyethylene terephthalate (PET), latex, thermoplastic elastomers and polyimides, as a few examples. Collars 101A-101D may be spaced apart by approximately 4 mm (e.g., with range of 2 mm and 6 mm). In some examples, collars 101A-101D may have a size that is approximately ⅓ the diameter of lead 90, but smaller and larger sizes are possible.

In some examples, the most distal collar (e.g., collar 101A) may be fixed in location (e.g., formed part of elongated member 93, welded or epoxied, as a few examples) on elongated member 93. The other collars (e.g., collars 101B-101D) may be slidable along elongated member 93. For example, as illustrated in FIG. 6A, collar 101A may form a first connection point for fixation members 100A and 100D and collar 101B may form a second connection point for fixation members 100A and 100D. Collar 101B may form a first connection point for fixation members 100B and 100E and collar 101C may form a second connection point for fixation members 100B and 100E. Collar 101C may form a first connection point for fixation members 100C and 100F and collar 101D may form a second connection point for fixation members 100C and 100F. Each of fixation members 100A-100F may be welded, bonded, or epoxied to respective ones of collar 101A-101D to connect to respective ones of collar 101A-101D.

Accordingly, in the example illustrated in FIGS. 6A-6D, collars 101A-101D are connected in series through respective fixation members 100A-100F. For example, collar 101A is connected to collar 101B through fixation members 100A and 100D, collar 101B is connected to collar 101C through fixation members 100B and 100E, and collar 101C is connected to collar 101D through fixation members 100C and 100F. Because collar 101A may be fixed in position on elongated member 93, collars 101B-101D are able to remain along the side of elongated member 93.

As described in more detail below, in some examples, when a longitudinal compression (e.g., pushing) force is applied to the most proximal collar (e.g., collar 101D), all fixation members 100A-100F have the same force exerted on them because fixation members 100A-100F are in series with each other. There may be some additional frictional forces or external forces from tissue when lead 90 is implanted causing the force exerted on each of fixation members 100A-100F to be different. However, such additional forces may be relatively minimal.

When a pushing force is applied to collar 101D, collars 101B-10D all move distally. As described above, collar 101A may be fixed in position. The movement of collars 101B-101D causes respective fixation members 100A-100F to bow outwards from elongated member 93. For instance, distal movement along elongated member 93 of collars 101D and 101C cause fixation members 100C and 100F to bow outwards, distal movement along elongated member 93 of collars 101C and 101B cause fixation members 100B and 100E to bow outwards, and distal movement along elongated member 93 of collar 101B with collar 101A being in fixed position causes fixation members 100A and 100D to bow outwards.

The amount that fixation members 100A-100F (also called bow-like members 100A-100F) bow outward may be based on the amount of distal movement of collars 101A-101D. For instance, FIGS. 6B-6D illustrate different amounts of movement of collars 101A-101D based on the different amount of distal movement of collars 101A-101D.

FIGS. 6B and 6C may be considered as illustrating fixation members 100A-100F in intermediate deployed states with the example illustrated in FIG. 6D being the final deployed state of fixation members 100A-100F. However, in some examples, the examples illustrated in FIG. 6B or 6C may be the final deployed state of fixation members 100A-100F. As one example, there may be one or more flanges or protrusions on elongated member 93 that stop how far distally collars 101B-101D can move. Other ways to limit the movement of collar 101B-101D are possible.

Once fixation members 100A-100F are deployed, the tissue from tongue 40 may provide sufficient friction so that collars 101B-101D do not move. Then, as scar tissue begins to form around and through the deployed fixation members 100A-100F, lead 90 may remain in place and collars 101B-101D may remain in place. In some examples, it may be possible to glue (e.g., surgical adhesive) or lock collars 101B-101D in place (e.g., deploy flanges on elongated member 93 to stop movement of collars 101B-101D along longitudinal axis 92 of elongated member 93) after fixation members 100A-100F are deployed to stop movement of collars 101B-101D until sufficient scarring tissue forms to hold lead 90 and collars 101B-101D in place.

FIGS. 6A-6D illustrate one example shape of fixation members 100A-100D. However, the techniques are not so limited. For instance, collars 101A-101D may be spaced apart at different distances so that the amount by which one of the fixation members 100A-100D bows out is different than the amount by which another one of the fixation members 100A-100D bows out. Also, in additional to fixation members 100A-100D that are bow-like fixation members, lead 90 may include tines (forward and/or backward facing) as fixation member.

As described above, one way to deploy fixation members 100A-100F is by applying a compression force to collar 101D. There may be various ways in which fixation members 100A-100F may transition from the undeployed state of FIG. 6A, through the first and second partially deployed states of FIGS. 6B and 6C, and to the fully deployed state of FIG. 6D, or to the deployed states of FIG. 6B or 6C, where the deployed states of FIG. 6B or 6C are the final, fully deployed state. As one example, the introducer used to implant lead 90 into tongue 40 may hold fixation members 100A-100F along elongated body 93. As the introducer is removed, fixation members 100A-100F expand out to the deployed state. For example, fixation members 100A-100F have a spring bias to naturally be in the deployed state illustrated in FIG. 6D. The introducer holds fixation members 100A-100F in the undeployed state and as the introducer is removed fixation members 100A-100F move to the deployed state due to the spring bias.

As another example, once lead 90 is secured in place, a push tubing may be used to push on collar 101D, and the force from the push tubing causes fixation members 100A-100F to deploy. In some examples, the push tubing may have a hydrophilic coating on the inner surface. Upon exposure to body fluids, the coating is hydrated, minimizing friction between the push tubing and the internal insulation of lead 90 to allow easier deployment of fixation members 100A-100F.

In some examples, the push tubing may be the introducer. For example, the introducer may initially cover fixation members 100A-100F, and then the introducer is pulled back proximally beyond collar 101D to expose fixation members 100A-100F. Then, the introducer is pushed distally and pushes collar 101D (e.g., applies a compression force to collar 101D), which compresses fixation members 100A-100F, and causes fixation members 100A-100F to extend. For instance, the introducer is first pulled back beyond collar 101D, and then rubs up against elongated member 93. As the introducer is moved distally along elongated member 93, the introducer moves collar 101D distally and the fixation members 100A-100F extend perpendicular to elongated member 93 since the introducer pushes up on collar 101D.

In this way, at least one fixation member of fixation members 100A-100F may be configured to deploy in response to movement of an introducer used for lead implantation. For example, the at least one fixation member of fixation members 100A-100F may be configured to deploy in response to the introducer pushing on the at least collar via elongated member 93 causing the at least one fixation member to distend perpendicular to lead 90.

The introducer may be an open grid and have "windows" that allow electrodes 98A and 98B on lead 90 to be exposed when lead 90 is even with the end of the introducer. In this way, the introducer does not have to be withdrawn to expose electrodes 98A and 98B, allowing for testing to ensure that lead 90 is properly placed before deployment of the fixation members 100A-100F. Having such windows in the introducer may reduce the chance of inadvertently deploying one or more fixation members 100A-100F during the testing to ensure proper lead placement.

As illustrated, in some examples, collar 101D includes opening 108. In some examples, a hook of a pushing device may be used to hook into opening 108. The surgeon may then push the pushing device distally causing collar 101D to move distally and apply the compression pressure to extend fixation members 100A-100F outward. In some examples, opening 108 may be used with a pulling device, which may be the same as the pushing device, to retract fixation members 100A-100F, as described below.

There may be more or fewer fixation members 100A-100F than illustrated in FIGS. 6A-6D. For ease of illustration, in FIGS. 6A-6D, fixation members 100A-100F are illustrated as being deployed along the x-axis, where the y-axis defines the longitudinal axis. In some examples, there may be additional fixation members that are deployed along the z-axis (e.g., fixation members like fixation members 100A-100F may extend at two points, three points, or four or more points around elongated member 93). For instance, there may be a plurality of fixation members located radially around elongated member 93. In some examples, the fixation members may be separated by approximately 90°.

Figure 7A:
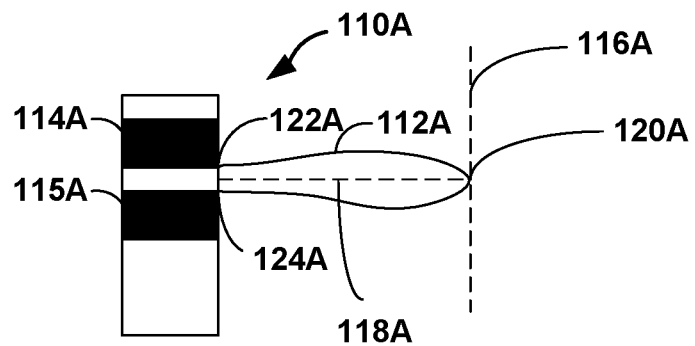
FIGS. 7A-7C are conceptual diagrams illustrating examples of deployed bow-like members.
Figure 7B:
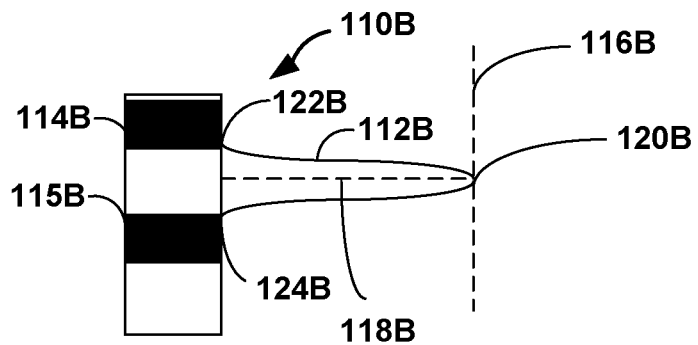
Figure 7C:
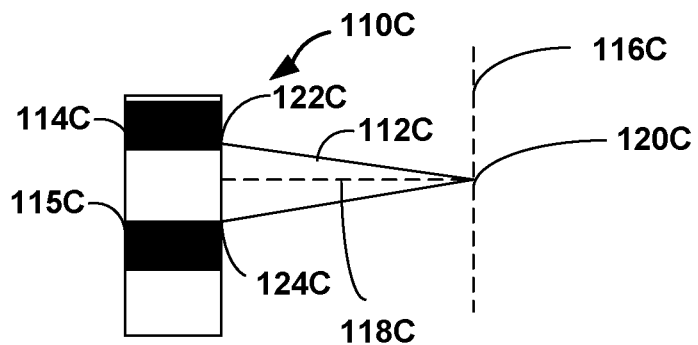

As illustrated in FIG. 6D, when deployed, at least one fixation member of fixation members 100A-100F includes a peak 102 that is substantially perpendicular to longitudinal axis 92 of elongated member 93 of lead 90, and represents the radially outermost portion of the fixation member relative to the longitudinal axis of elongated member 93. Peak 102 is illustrated in FIG. 6D to ease with illustration, and there are respective peaks on other fixation members 100A-100F. Also, there is a peak for respective fixation members 100A-100F illustrated in FIGS. 6B and 6C. FIGS. 7A-7C illustrate the example of peaks in further detail.

As one example, peak 102 refers to a location on fixation member 100A-100F having at least two connections back to respective collars 101A-101D, where the tangent line at peak 102 is parallel to lead 90 (e.g., longitudinal axis 92). For example, peak 102 is on fixation member 100E having a first connection point on collar 101A and a second connection point on collar 101B. Peak 102 may be a point of fixation member 100E that is furthest from elongated member 93 (e.g., an outward most bend of fixation member 100E). A tangent line at the point of peak 102 may be parallel with longitudinal axis 92. Further, a line extending from peak 102 to elongated member 93 may be substantially perpendicular to longitudinal axis 92 and intersect elongated member 93 substantially midway between the first connection point and the second connection point. As noted above, FIGS. 7A-7C further illustrates examples of peaks.

For example, in examples where one or more fixation members 100A-100F are lobe shaped, as illustrated in FIG. 6D, peak 102 may be the highest point on the arc of the lobes. In such examples, there is an arc towards peak 102, which forms one of the connections to collar 101B, and an arc away from peak 102, which forms another of the connections to collar 101A. In examples where one or more of fixation members 100A-100F are triangular shaped, there may be two points respectively on two collars 101A-101D that define a width of the triangle, and the third point connects to the two points and forms a peak, as illustrated by peak 33 in FIG. 2. "Substantially perpendicular" means that a line extending from the peak is within a range of 75° to 105°, and generally at 90° relative to the longitudinal axis of the elongated member 93 (e.g., leady body) of lead 90.

A distance 104 between lead 90 and peak 102 of the at least one fixation member of fixation members 100A-100F may be approximately 2 mm (e.g., between a range of 1.5 mm and 2.5 mm). In some examples, the distance 104 may be approximately twice the diameter of lead 90. Because lead 90 is implanted in musculature of tongue 40, there would be eventual tissue scaring from the operation, which may scar around fixation members 100A-100F that are extended outwards and embedded in or against the tissue. The tissue scarring may already provide some level of securing lead 90 in place (e.g., to minimize lead migration). Therefore, having large sized fixation members may not be necessary. For example, by having fixation members 100A-100F extend approximately 2 mm outward from lead 90, there may be sufficient anchoring of lead 90 to the musculature to minimize lead migration as the bow-like members (e.g., arc-shaped, triangular-shaped, or lobe-shaped bow-like members embed in or bear against the tissue of tongue 40). Some other lead types, such as those implanted intravenously, may require larger sized fixation members to anchor to the blood vessels because scar tissue is not available. However, in one or more examples described in this disclosure, there may be scarring of the tissue of tongue 40 allowing for smaller sized fixation members 100A-100F (e.g., such that distance 104 from peak 102 to lead 90 is approximately 2 mm).

In the example of FIGS. 6A-6D, there may be only two electrodes 98A and 98B, rather than four electrodes 30, like FIG. 2. Having fewer electrodes at distal end 94 allows for fixation members, like fixation members 100A-100F, to be closer to distal end 94, thereby increasing the number of fixation members 100A-100F that are deployed within tongue 40. For instance, if fixation members 100A-100F were more proximate to distal end 94, then there is a possibility that none of fixation members 100A-100F will be implanted within tissue of tongue 40. For example, by having less than four electrodes, it may be possible that a distance 106 from distal end 94 of lead 90 and the most proximal fixation member (e.g., fixation members 100C and 100F) is less than or equal to 10 mm.

In some examples, the diameter of lead 90 is less than 1.5 mm. For example, the diameter of lead 90 may be approximately 3.8 Fr (French), which is approximately 1.27 mm. Diameter sizes greater than 1.5 mm may be possible. However, having the diameter of lead 90 less than 1.5 mm may be desirable. For example, because lead 90 is to be implanted within musculature of tongue 40, there should be sufficient tissue surrounding lead 90 to ensure that lead 90 stays in place, especially after fixation members 100A-100F are deployed. Some other lead types, such as those used intravenously, may require wider diameter, such as 5 Fr, which is approximately 1.67 mm, to ensure that when its fixation members are deployed, that the lead stays within the blood vessels. With the anatomical structure of tongue 40 being different than veins and with lead 90 being implanted in musculature, instead of vasculature, having wider diameter leads may not be needed, and in some cases may negatively impact the functionality of the lead. For instance, as described above, due to movement of tongue 40, especially as compared to movement of vasculature, there may be benefits with ensuring high flexibility of lead 90. By having a thinner diameter (e.g., 3.8 Fr instead of 5 Fr), there may be an increase in flexibility of lead 90.

In some cases, fixation members 100A-100F may be permanently deployed. However, there may be cases where fixation members 100A-100F need not be permanently deployed. For instance, once lead 90 is deployed, lead 90 may be re-positioned after surgery or after trialing period. To address this, in some examples, tines may be used (e.g., in addition to bow-like fixation members). The tines may be deployed but the bow-like fixation members may not be deployed until determining that no further lead repositioning is needed.

However, it may be possible to deploy the bow-like fixation members such as where the bow-like fixation members are retractable (e.g., using a pulling tubing that pulls the fixation members back to the body of lead 90). For example, FIGS. 6A-6D illustrate opening 108 in collar 101D. In some examples, to retract fixation members 100A-100F, a hook of a pulling device is inserted in to opening 108 and the pulling device is pulled back proximally to retract fixation members 100A-100F.

In the above examples, collar 101A is described as being fixed and collar 101D is described as having opening 108. However, the example techniques are not so limited. In some examples, collar 101A may include opening 108 and collar 101D may be fixed. In such examples, a pushing member may be inserted from distal end 94 to apply the compression pressure or a hook of the pushing device may be put into opening 108 and used to push collar 101A proximally to apply the compression pressure. A pulling device, which may be same as pushing device, may be used to hook into opening 108, in examples where opening 108 is on collar 101A, and pulled distally to retract fixation members 100A-100F.

To allow repositioning, in some examples, the tines may not be one-directional. That is, a tine can rotate 180° from a joint at lead 90. For example, a tine may be initially pointed towards proximal end 96 and can be rotated such that the tine can point towards distal end 94. In some examples, the tines can be perpendicular to lead 90 by extending directly radially without being angled in an orientation opposite of entry. In this way, there may not be a "fish hook" effect, allowing lead 90 to be moved proximal or distal without the tines digging into tissue.

There could additionally or alternatively be a mechanical fixation of the tine or the tines may be in the form of a "screw thread" enabling insertion and retraction by twisting lead 90. Another type of removable fixation member may have the tines curved around the circumference of the electrode shaft. Turning in one direction would deploy, and in other direction retract the tines. The benefit may be less tissue trauma during removal, re-positioning, or replacement of the lead after scaring of the tissue.

In some examples, once fixation members 100A-100F (e.g., bow-like fixation members being arc shape, triangular shaped, or lobe shaped, and/or tines) are deployed, extraction of lead 90 may be problematic, whether part of intraoperative or post-surgery. To ease extraction, in some examples, fixation members 100A-100F may be retractable or made to dissolve to avoid trauma to the patient during any movement of lead 90. Accordingly, in some examples, one or more of the one or more fixation members 100A-100F are configured to be retractable. Additionally or alternatively, one or more of the one or more fixation members 100A-100F may be configured to dissolve after deployment. Examples of fixation members 100A-100F that dissolve include aresynthetic polymer materials, such as polydioxanone, polyglycolic acid, polyglyconate, and polylactic acid (e.g., PL Poly(L-Iactide), PC Poly(ε-caprolactone), PLC Poly(L-Iactide/ε-caprolactone), PLG Poly(L-Iactide/Glycolide), PDL Poly(DL-Iactide), PLDL Poly(L-DL Iactide), and PG Poly(Glycolide). As described above, scarring of tissue of tongue 40 may fix lead 90 in place. Accordingly, even if fixation members 100A-100F are retracted or dissolved, the chances of lead 90 migrating may be minimal.

FIGS. 7A-7C are conceptual diagrams illustrating examples of deployed bow-like members. FIG. 7A illustrates lead 110A, which is similar to leads 20 and 90. Lead 110A includes collars 114A and 115A and bow-like member 112A. Initially, collars 114A and 115A may be further apart from one another, and bow-like member 112A may rest along the elongated member of lead 110A. In response to a compression force (e.g., pushing or pulling), collars 114A and 115A come closer together and bow-like member 112A bows out to form a lobe shape illustrated in FIG. 7A.

As illustrated, bow-like member 112A connects to collar 114A at first connection point 122A and to collar 115A at second connection point 124A. Bow-like member 112A may be epoxied, formed as part of, crimped, welded, soldered, or the like to first connection point 122A and second connection point 124A.

When deployed, bow-like member 112A defines peak 120A. Peak 120A may be point of bow-like member 112A that is furthest from the elongated member of lead 110A. In some examples, tangent line 116A at the point of peak 120A is parallel with the longitudinal axis of lead 110A (e.g., parallel with lead 110A). Also, line 118A extending from peak 120A to the elongated member of lead 110A may be substantially perpendicular to the longitudinal axis (e.g., substantially perpendicular to elongated member of lead 110A). In some examples, line 118A may intersect the elongated member of lead 110A substantially midway (e.g., halfway) between first connection point 122A and second connection point 124B. That is, line 118A that intersects lead 110A and peak 120A crosses the midway point between first connection point 122A and second connection point 124A. As illustrated, there is only one peak 120A between first connection point 122A and second connection point 124A. In some examples, the length of line 118A is approximately 2 mm. In some examples, the ratio of the length of line 118A to the diameter of lead 110A may be approximately 1.5 (e.g., 1.3 to 1.8) or approximately 2 (e.g., 1.8 to 2.2).

FIG. 7B illustrates lead 110B, which is similar to leads 20 and 90. Lead 110B includes collars 114B and 115B and bow-like member 112B. Initially, collars 114B and 115B may be further apart from one another, and bow-like member 112B may rest along the elongated member of lead 110B. In response to a compression force (e.g., pushing or pulling), collars 114B and 115B come closer together and bow-like member 112B bows out to form an arc shape illustrated in FIG. 7B.

As illustrated, bow-like member 112B connects to collar 114B at first connection point 122B and to collar 115B at second connection point 124B. Bow-like member 112B may be epoxied, formed as part of, crimped, welded, soldered, or the like to first connection point 122B and second connection point 124B.

When deployed, bow-like member 112B defines peak 120B. Peak 120B may be point of bow-like member 112B that is furthest from the elongated member of lead 110B. In some examples, tangent line 116B at the point of peak 120B is parallel with the longitudinal axis of lead 110B (e.g., parallel with lead 110B). Also, line 118B extending from peak 120B to the elongated member of lead 110B may be substantially perpendicular to the longitudinal axis (e.g., substantially perpendicular to elongated member of lead 110B). In some examples, line 118B may intersect the elongated member of lead 110B substantially midway (e.g., halfway) between first connection point 122B and second connection point 124B. That is, line 118B that intersects lead 110B and peak 120B crosses the midway point between first connection point 122B and second connection point 124B. As illustrated, there is only one peak 120B between first connection point 122B and second connection point 124B. In some examples, the length of line 118B is approximately 2 mm. In some examples, the ratio of the length of line 118B to the diameter of lead 110B may be approximately 1.5 (e.g., 1.3 to 1.8) or approximately 2 (e.g., 1.8 to 2.2).

FIG. 7C illustrates lead 110C, which is similar to leads 20 and 90. Lead 110C includes collars 114C and 115C and bow-like member 112C. Initially, collars 114C and 115C may be further apart from one another, and bow-like member 112C may rest along the elongated member of lead 110C. In response to a compression force (e.g., pushing or pulling), collars 114C and 115C come closer together and bow-like member 112C bows out to form a triangular shape illustrated in FIG. 7C.

As illustrated, bow-like member 112C connects to collar 114C at first connection point 122C and to collar 115C at second connection point 124C. Bow-like member 112C may be epoxied, formed as part of, crimped, welded, soldered, or the like to first connection point 122C and second connection point 124C. To form a triangular shape, there may be a joint at the midway point between first connection point 122C and second connection point 124C that defines two segments of bow-like member 112C. For instance, a first segment is from first connection point 122C to the joint and a second segment is from second connection point 124C to the joint. As the compression force is applied, the joint moves outward to define peak 120C.

When deployed, bow-like member 112C defines peak 120C. Peak 120C may be point of bow-like member 112C that is furthest from the elongated member of lead 110C. In some examples, tangent line 116C at the point of peak 120C is parallel with the longitudinal axis of lead 110C (e.g., parallel with lead 110C). Also, line 118C extending from peak 120C to the elongated member of lead 110C may be substantially perpendicular to the longitudinal axis (e.g., substantially perpendicular to elongated member of lead 110C). In some examples, line 118C may intersect the elongated member of lead 110C substantially midway (e.g., halfway) between first connection point 122C and second connection point 124C. That is, line 118C that intersects lead 110C and peak 120C crosses the midway point between first connection point 122C and second connection point 124C. As illustrated, there is only one peak 120C between first connection point 122C and second connection point 124C. In some examples, the length of line 118C is approximately 2 mm. In some examples, the ratio of the length of line 118C to the diameter of lead 110C may be approximately 1.5 (e.g., 1.3 to 1.8) or approximately 2 (e.g., 1.8 to 2.2).

Figure 8:
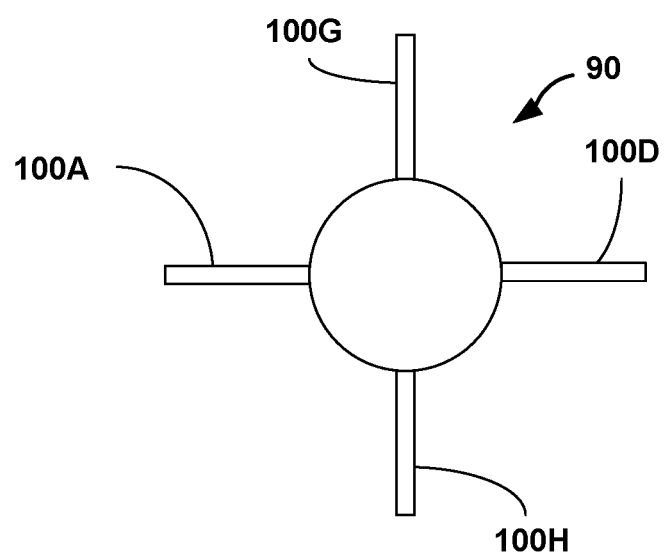
FIG. 8 is a top perspective of a lead with deployed fixation members.

FIG. 8 is a top perspective of a lead with deployed fixation members. As described above, in some examples, there may be a plurality of fixation members located at different circumferential positions around elongated member 93 of lead 90. FIG. 8 illustrates an example of plurality of fixation members that extend radially outward from elongated member 93 and located around elongated member 93 at different circumferential positions. For instance, similar to FIGS. 6A-6D, FIG. 8 illustrates fixation members 100A and 100D. In addition, FIG. 8 illustrates fixation members 100G and 100H. Fixation members 100G and 100H may be similar to fixation members 100A and 100D and may located at the same axial level as fixation members 100A and 100D, but at different circumferential positions about the outer surface of the lead body, e.g., separated from one another in the example of FIG. 8 by approximately 90°. Although four fixation members are illustrated in FIG. 8, in some examples, there may be fewer (e.g., three, two, or one) or greater (e.g., more than four) fixation members. The width of each of fixation members 100A, 100D, 100G, and 100H, as well as 100B, 100C, 100E, and 100F may be less than 2 mm, and possibly within a range of 0.5 mm to 1.5 mm but widths greater than 2 mm are possible as well. In some examples, the width of each of fixation members 100A-100H may be approximately one-tenth, one-fifth, or one-third the diameter of lead 90.

Figure 9A:
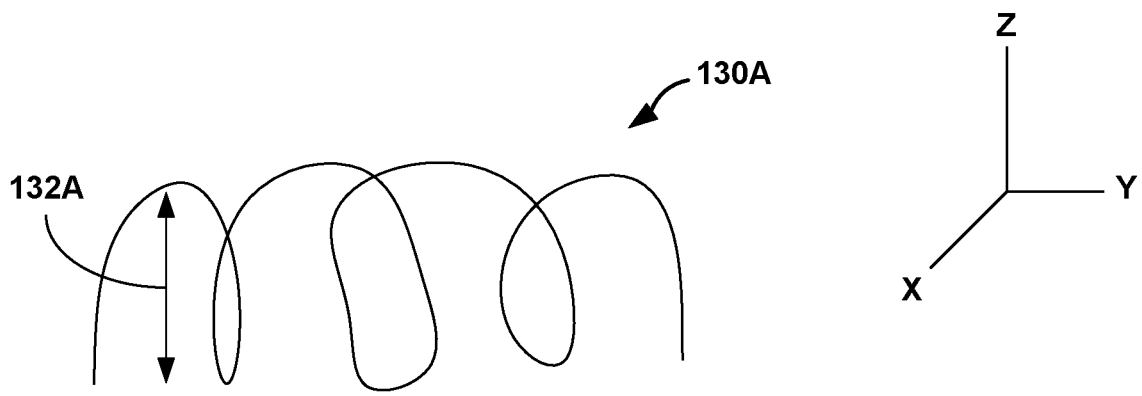
FIGS. 9A-9C are conceptual diagrams illustrating lead position after implantation.
Figure 9B:
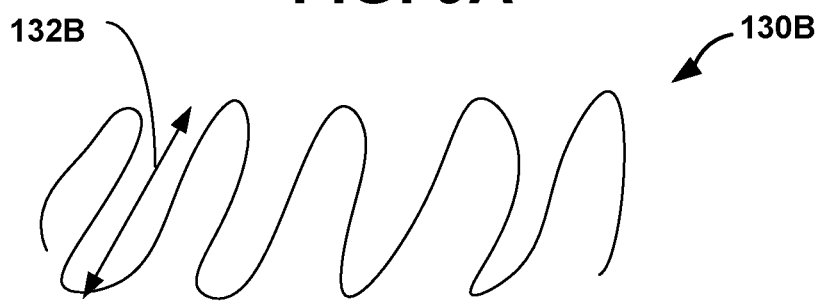
Figure 9C:
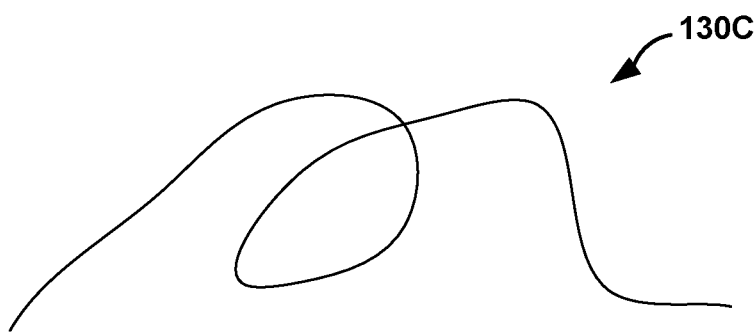

FIGS. 9A-9C are conceptual diagrams illustrating lead position after implantation. When tongue 40 is extended and retracted, there may be stress causing breakage of leads 20, 90, or 110A-100C or discomfort to patient 14. In some examples, leads 20, 90, or 110A-110C may be implanted in a way to allow stress relief, as well as avoid kinking. For examples, FIGS. 9A-9C illustrate examples of lead positions 130A-130C, respectively. In FIGS. 9A-9C, the leads are orientated along the proximal to distal axis of tongue 40 (e.g., y-axis) and along the lateral axis of tongue 40 (e.g., x-axis).

FIGS. 9A-9C illustrate examples to ease with understanding and should not be considered limiting. For instance, for leads 20, 90, or 110A-110C, there are two portions: a first portion that is in tissue of tongue 40 and a second portion that is tunneled subcutaneously to IMD 16. There may be relatively small curvature in the first portion. For instance, the amplitude of the curvature, shown by amplitude 132A and 132B, may be approximately 5 to 6 mm. In the second portion, the amplitude of the curvature may be greater, such as 10 to 20 mm.

Also the numbers of curves shown in FIGS. 9A and 9B (e.g., where a curve is peak or a bend in the lead) may be approximately 1 to 3 curves (although more are possible as shown in FIGS. 9A and 9B), which are spread out over 2 to 3 cm, within the first portion (e.g., part of the in tongue 40).

The number of curves in the second portion of the lead (e.g., tunneled to IMD 16 through neck) may be 2 to 6 curves spread out over 10 to 20 cm.

FIG. 9A illustrates an example of lead position 130A as a helix or compound helix. In the example of FIG. 9A, lead position 130A may have a property that a tangent line at any point makes a substantial constant angle with an axis. For instance, lead position 130A may be similar to a coil spring or spiral staircase. A helix may be considered as a single coil, and a compound helix may be considered as taking a single coil and wrapping it into a larger coil. For example, a compound helix is lead 20, 90, or 110A-110C curved to form a plurality of helixes, and the plurality of helixes are curved to form a compound helix (e.g., a compound helix is a plurality of helixes curved to form a helix). The resulting structure is very flexible in the axial direction. If lead 20, 90, or 110A-110C is made from this construction, the helix or compound helix structure reduces the axial load on lead 20, 90, or 110A-110C, reducing the likelihood of breakage or dislodgement FIG. 9B illustrates an example of lead position 130B as a wave shape. In the example of FIG. 9B, lead position 130B may have a property that the lead forms a sinusoidal or sinusoidal-like shape once implanted. In some examples, rather than a sinusoidal shape, the lead may be implanted in a saw-tooth shape.

FIG. 9C illustrates an example of lead position 130C where a loop is included in the lead after implantation. The location of the loop may generally be at any location along the lead body. The size of the loop may be based on factors such as size of lead and discomfort to patient 14.

Although FIGS. 9A-9C are illustrated separately, one or more of the examples of FIGS. 9A-9C may be used together. For example, a loop may be included in the sinusoidal shape of the lead.

In general, shapes for stress relief of the lead include a helix, a compound helix, a wave or saw-tooth shape or even putting a loop into the lead when relaxed. Electrodes 30 or 98A, 98B may be placed distal or more proximal depending on the amount of relief desired. Extension of tongue 40 can move the electrodes away from or toward the hypoglossal nerve and/or motor points 54A, 54B, 55A, and/or 55B depending on the location of the stress relief pattern or position of lead. Moreover, variations in placement of the saw-tooth stress relief or the electrodes can enable the lead to maintain functioning after some amount of displacement or movement.

Figure 10:
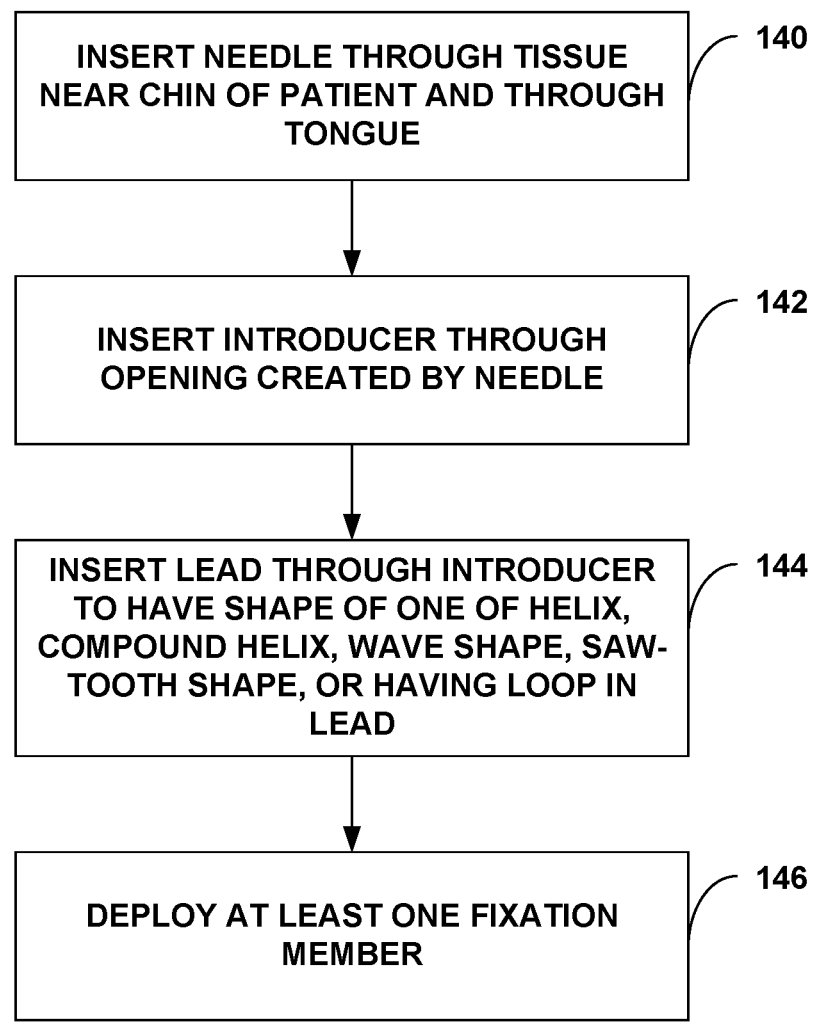
FIG. 10 is a flowchart illustrating an example of lead implantation.

FIG. 10 is a flowchart illustrating an example of lead implantation. A medical professional may insert a needle through tissue near a chin of patient 14 and through tongue 40 of patient 14 (140). By inserting the needle, the medical professional creates an opening for placement of a lead like lead 20, 90, or 110A-110C. The medical professional may insert an introducer through an opening created by the needle (142).

The medical professional may insert a lead (e.g., lead 20, 90, or 110A-110C) through the introducer to have a shape of one of a helix, a compound helix, a wave shape, or saw-tooth shape, or having a loop in the lead implanted in tongue 40 (144). As described above, lead 20, 90, or 110A-110C may include an elongated member and one or more electrodes at a distal end of the elongated member such that the one or more electrodes are implanted proximate to one or more motor points (e.g., motor points 54A, 54B, 55A, and/or 55B) of a protrusor muscle (e.g., at least one of the genioglossal or geniohyoid muscle) within tongue 40 of patient 14.

The medical professional may deploy at least one fixation member of the one or more fixation members (e.g., 32, 100A-100F, or 112A-112C) (146). The at least one fixation member may be a bow-like member that, when deployed, defines a peak (e.g., peak 33, 102, or 120A-120C) between a first connection point on a first collar (e.g., collar 101A-101D, 114A, 114B, 115A, 115B, 115C, or 115C) and a second connection point on a second collar (e.g., collar 101A-101D, 114A, 114B, 115A, 115B, 115C, or 115C) of the bow-like member. In some examples, the medical professional may deploy the at least one fixation member based on movement of the introducer. For example, the introducer may hold fixation members 100A-100F along the body of lead 90 and proximal movement of the introducer may cause fixation members 100A-100F to deploy (e.g., due to spring bias). As another example, the medical professional may pull back the introducer proximally to be more proximal than fixation members 100A-100F, and then push the introducer distally to apply compression pressure to distal collar 101D and cause fixation members 100A-100F to distend perpendicularly.

It should be noted that system 10, and the techniques described herein, may not be limited to treatment or monitoring of a human patient. In alternative examples, system 10 may be implemented in non-human patients, e.g., primates, canines, equines, pigs, and felines. These other animals may undergo clinical or research therapies that my benefit from the subject matter of this disclosure. Various examples are described herein, such as the following examples.

Example 1: A lead for delivering electrical stimulation therapy, the lead comprising an elongated member defining a longitudinal axis and comprising a proximal end and a distal end, one or more electrodes disposed at the distal end of the elongated member, a plurality of collars located along the longitudinal axis of the elongated member, and one or more fixation members, wherein at least one of the fixation members is a bow-like member having a first connection point to a first collar of the plurality of collars and a second connection point to a second collar of the plurality of collars, wherein the distal end of the elongated member is configured for insertion in a tongue of a patient such that the one or more electrodes are implanted proximate to one or more motor points of a protrusor muscle within the tongue of the patient and the bow-like member of the one or more fixation members is implanted within tissue of the tongue, and wherein the bow-like member, when deployed, defines a peak between the first connection point and the second connection point of the bow-like member, and wherein the peak is a point of the bow-like member that is furthest from the elongated member.

Example 2. The lead of example 1, wherein a tangent line at the point of the peak is parallel with the longitudinal axis, and wherein a line extending from the peak to the elongated member is substantially perpendicular to the longitudinal axis and intersects the elongated member substantially midway between the first connection point and the second connection point.

Example 3. The lead of any of examples 1 and 2, wherein the one or more fixation members, when deployed, comprise a triangular shape or a lobe shape.

Example 4. The lead of any of examples 1-3, wherein a distance between the elongated member and the peak of the bow-like member is approximately 2 millimeter (mm).

Example 5. The lead of any of examples 1-4, wherein a diameter of the lead is less than 1.5 mm.

Example 6. The lead of any of examples 1-5, wherein a distance between the distal end of the lead and the bow-like member is less than or equal to 10 mm.

Example 7. The lead of any of examples 1-6, wherein the one or more electrodes comprise less than four electrodes.

Example 8. The lead of any of examples 1-7, wherein the bow-like member is configured to deploy in response to movement of an introducer used for lead implantation.

Example 9. The lead of example 8, wherein the bow-like member is configured to deploy in response to the introducer pushing on a distal collar of the plurality of collars.

Example 10. The lead of any of examples 1-9, wherein one or more of the one or more fixation members are configured to be retractable.

Example 11. The lead of any of examples 1-10, wherein one or more of the one or more fixation members are configured to dissolve after deployment.

Example 12. The lead of any of examples 1-11, wherein the lead is configured to have flexibility to form a shape of a helix, a compound helix, a wave shape, a saw-tooth shape, or include a loop in the lead after implantation.

Example 13. A system for delivering electrical stimulation therapy, the system comprising a lead for delivering electrical stimulation therapy, the lead comprising an elongated member defining a longitudinal axis and comprising a proximal end and a distal end, one or more electrodes disposed at the distal end of the elongated member, a plurality of collars located along the longitudinal axis of the elongated member, and one or more fixation members, wherein at least one of the fixation member is a bow-like member having a first connection point to a first collar of the plurality of collars and a second connection point to a second collar of the plurality of collars, wherein the distal end of the elongated member is configured for insertion in a tongue of a patient such that the one or more electrodes are implanted proximate to one or more motor points of least one of a genioglossal or geniohyoid muscle within the tongue of the patient and the bow-like member of the one or more fixation members is implanted within tissue of the tongue, and wherein the bow-like member, when deployed, defines a peak between the first connection point and the second connection point of the bow-like member, and wherein the peak is a point of the bow-like member that is furthest from the elongated member, and a medical device comprising a connector assembly configured to couple to the proximal end of the elongated member of the lead, wherein the medical device is configured to deliver electrical stimulation therapy via the one or more electrodes that cause at least one of the genioglossal or geniohyoid muscle to protrude the tongue of the patient.

Example 14. The system of example 13, wherein the lead comprises a first lead comprising a first elongated member defining a first longitudinal axis and comprising a first proximal end and a first distal end, a first set of one or more electrodes, a first plurality of collars, and a first set of one or more fixation members, wherein the bow-like member comprises a first bow-like member, wherein the protrusor muscle is a first protrusor muscle, and wherein the one or more motor points comprises a first set of motor points, the system further comprising a second lead comprising a second elongated member defining a second longitudinal axis and comprising a second proximal end and a second distal end, a second set of one or more electrodes disposed at the distal end of the second elongated member, a second plurality of collars located along the second longitudinal axis of the elongated member, and a second set of one or more fixation members, wherein at least one of the second set of fixation members is a second bow-like member having a first connection point to a first collar of the second plurality of collars and a second connection point to a second collar of the second plurality of collars, wherein the second distal end of the second elongated member is implanted in the tongue of the patient such that the second set of one or more electrodes are implanted proximate to a second set of motor points of a second protrusor muscle within the tongue of the patient and the second bow-like member is implanted within tissue of the tongue, and wherein the second bow-like member, when deployed, defines a peak between the first connection point to the first collar of the second plurality of collars and the second connection point to the second collar of the second plurality of collars of the second bow-like member, and wherein the second peak is a point of the second bow-like member that is furthest from the second elongated member.

Example 15. The system of any of examples 13 and 14, wherein at least one of a distance between the lead and the peak of the at least one fixation member is approximately 2 millimeter (mm), a diameter of the lead is less than 1.5 mm, and a distance between the distal end of the lead and the at least one fixation member is less than or equal to 10 mm.

Example 16. The system of any of examples 13-15, wherein the one or more electrodes comprise less than four electrodes.

Example 17. The system of any of examples 13-16, wherein the one or more fixation member, when deployed, comprise a triangular shape or a lobe shape.

Example 18. The system of any of examples 13-17, wherein one or more of the one or more fixation members are configured to, at least one of, be retractable or dissolve after deployment.

Example 19. A lead for delivering electrical stimulation therapy, the lead comprising an elongated member defining a longitudinal axis and comprising a proximal end and a distal end, wherein the elongated member has a diameter less than 1.5 millimeter (mm), one or more electrodes disposed at the distal end of the elongated member, a plurality of collars located along the longitudinal axis of the elongated member, and one or more fixation members, wherein at least one of the fixation members is a bow-like member having a first connection point to a first collar of the plurality of collars and a second connection point to a second collar of the plurality of collars, and wherein the one or more fixation members, when deployed, comprise a triangular shape or a lobe shape, wherein the distal end of the elongated member is configured for insertion in a tongue of a patient such that the one or more electrodes are implanted proximate to one or more motor points of a protrusor muscle within the tongue of the patient and the bow-like member of the one or more fixation members is implanted within tissue of the tongue, and wherein the bow-like member, when deployed, defines a peak between the first connection point and the second connection point of the bow-like member, and wherein the peak is a point of the bow-like member that is furthest from the elongated member, wherein a distance between the lead and the peak of the bow-like member is approximately 2 millimeter, and wherein a distance between the distal end of the elongated member and the bow-like member is less than or equal to 10 mm.

Example 20. The lead of example 19, wherein the one or more electrodes comprise less than four electrodes.

Example 21. The lead of any of examples 19 and 20, wherein the bow-like member is configured to deploy in response to movement of an introducer used for lead implantation.

Example 22. The lead of any of examples 19-21, wherein one or more of the one or more fixation members are at least one of configured to be retractable or configured to dissolve after deployment.

Example 23. The lead of any of examples 19-22, wherein the lead is configured to have flexibility to form a shape of a helix, a compound helix, a wave shape, a saw-tooth shape, or include a loop in the lead after implantation.

Example 24. A method of implanting a lead, the method comprising inserting a needle through tissue near a chin of a patient and through a tongue of the patient, inserting an introducer through an opening created by the needle, and inserting a lead through the introducer, the lead comprising an elongated member and one or more electrodes at a distal end of the elongated member such that the one or more electrodes are implanted proximate to one or more motor points of a protrusor muscle within the tongue of the patient, wherein inserting the lead comprises inserting the lead to have a shape of one of a helix, a compound helix, a wave shape, or saw-tooth shape, or having a loop in the lead.

Example 25. The method of example 24, deploying at least one fixation member of the one or more fixation members, wherein the at least one fixation member, when deployed, defines a peak between a first connection point on a first collar on the lead and a second connection point on a second collar on the lead, and wherein the peak is a point of the at least one fixation member that is furthest from the elongated member.

Example 26. The method of example 25, wherein deploying the at least one fixation member comprises deploying the at least one fixation member based on movement of the introducer.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processing circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. For example, any module described herein may include electrical circuitry configured to perform the features attributed to that particular module, such as fixed function processing circuitry, programmable processing circuitry, or combinations thereof.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method of implanting a lead, the method comprising:
inserting a needle through tissue near a chin of a patient and through a tongue of the patient;
inserting an introducer through an opening created by the needle;
inserting the lead through the introducer, the lead comprising one or more fixation members, an elongated member, and one or more electrodes in a distal portion of the elongated member such that the one or more electrodes are implanted proximate to one or more motor points of a protrusor muscle within the tongue of the patient, wherein inserting the lead comprises inserting the lead to have a shape of one of a helix, a compound helix, a wave shape, or saw-tooth shape, or to have a loop in the lead; and deploying at least one fixation member of the one or more fixation members, wherein the at least one fixation member, when deployed, defines a peak between a first connection point on a first collar of a plurality of collars on the lead and a second connection point on a second collar of the plurality of collars on the lead, and wherein the peak is a point of the at least one fixation member that is furthest from the elongated member upon the deployment of the at least one fixation member.

2. The method of claim 1, wherein deploying the at least one fixation member comprises deploying the at least one fixation member based on movement of the introducer.

3. The method of claim 1, wherein deploying the at least one fixation member comprises deploying the at least one fixation member based on the introducer pushing on a distal collar of the plurality of collars.

4. The method of claim 1, wherein deploying the at least one fixation member comprises deploying the at least one fixation member based on the introducer holding the at least one fixation member along the elongated member, and proximal movement of the introducer past the at least one fixation member to cause the at least one fixation member to deploy.

5. The method of claim 1, further comprising retracting the at least one fixation member.

6. The method of claim 1, wherein the one or more fixation members, when deployed, comprise a triangular shape or a lobe shape.

7. The method of claim 1, wherein a distance between the elongated member and the peak is approximately 2 millimeter (mm).

8. The method of claim 1, wherein the one or more electrodes comprise less than four electrodes.

9. The method of claim 1, wherein a diameter of the lead is less than 1.5 mm.

10. The method of claim 1, further comprising:
inserting a guidewire through the needle;
anchoring the guidewire to tissue of the tongue; and
removing the needle,
wherein inserting the introducer through the opening created by the needle comprises placing the introducer over the guidewire through the opening created by the needle.

11. The method of claim 1, further comprising:
tunneling a proximal port of the lead back to connection with an implantable medical device (IMD); and
connecting the lead to the IMD.

12. The method of claim 11, further comprising:
causing the IMD to deliver electrical stimulation to the motor points.

13. The method of claim 1, wherein the motor points of the protrusor muscles are of a hypoglossal nerve.

14. The method of claim 1, wherein the motor points are of a first hypoglossal nerve, and wherein the lead comprises a first lead, the method further comprising inserting a second lead proximate to motor points of a second hypoglossal nerve.

15. The method of claim 1, wherein the one or more electrodes in the distal portion of the elongated member comprise one or more ring electrodes around the distal portion of the elongated member.

* * * * *